United States Patent
Flügel et al.

(10) Patent No.: US 11,643,696 B2
(45) Date of Patent: May 9, 2023

(54) **METHOD FOR DETECTING *C. PERFRINGENS* INDUCED DISEASES IN ANIMALS**

(71) Applicant: EVONIK OPERATIONS GMBH, Essen (DE)

(72) Inventors: Monika Flügel, Steinhagen (DE); Stefan Pelzer, Gütersloh (DE); Filip Van Immerseel, Eke (BE); Richard Ducatelle, Wortegem-Petegem (BE); Evy Goossens, Wachtebeke (BE); Sarah Hark, Gütersloh (DE); Frank Thiemann, Nottuln (DE); Florian Böhl, Neckargemünd (DE)

(73) Assignee: Evonik Operations GmbH, Essen (DE)

( * ) Notice: Subject to any disclaimer, the term of this patent is extended or adjusted under 35 U.S.C. 154(b) by 194 days.

(21) Appl. No.: 16/612,398

(22) PCT Filed: May 9, 2018

(86) PCT No.: PCT/EP2018/062090
§ 371 (c)(1),
(2) Date: Nov. 10, 2019

(87) PCT Pub. No.: WO2018/206690
PCT Pub. Date: Nov. 15, 2018

(65) Prior Publication Data
US 2021/0139955 A1    May 13, 2021
US 2022/0025439 A9    Jan. 27, 2022

Related U.S. Application Data

(60) Provisional application No. 62/531,000, filed on Jul. 11, 2017.

(30) Foreign Application Priority Data

May 12, 2017   (EP) .................................... 17170811
Aug. 1, 2017   (CN) ............................. 201710646838

(51) Int. Cl.
*C12Q 1/68*      (2018.01)
*C12Q 1/689*     (2018.01)
*C12Q 1/686*     (2018.01)

(52) U.S. Cl.
CPC ............ *C12Q 1/689* (2013.01); *C12Q 1/686* (2013.01)

(58) Field of Classification Search
CPC ................................. C12Q 1/689; C12Q 1/686
See application file for complete search history.

(56) References Cited

U.S. PATENT DOCUMENTS

| | | |
|---|---|---|
| 5,538,851 A | 7/1996 | Fach et al. |
| 5,874,220 A * | 2/1999 | Fach ...................... C07K 14/33 435/6.12 |
| 6,812,023 B1 | 11/2004 | Lamparski et al. |
| 6,899,863 B1 | 5/2005 | Dhellin et al. |
| 7,198,923 B1 | 4/2007 | Abrignani et al. |
| 7,374,927 B2 | 5/2008 | Palma et al. |
| 8,263,088 B2 | 9/2012 | Moore et al. |
| 8,673,560 B2 | 3/2014 | Leamon et al. |
| 2003/0050470 A1 * | 3/2003 | An ......................... C07K 14/82 536/24.3 |
| 2004/0101860 A1 | 5/2004 | Jones et al. |
| 2007/0042354 A1 | 2/2007 | Engelhard et al. |
| 2010/0291131 A1 | 11/2010 | Moore et al. |
| 2012/0058904 A1 | 3/2012 | Shanks et al. |
| 2014/0099373 A1 | 4/2014 | Broomhead et al. |
| 2014/0178885 A1 | 6/2014 | Park et al. |
| 2016/0041153 A1 | 2/2016 | Brown et al. |
| 2017/0108503 A1 | 4/2017 | Klass et al. |
| 2018/0312905 A1 | 11/2018 | Igwe |

(Continued)

FOREIGN PATENT DOCUMENTS

| | | |
|---|---|---|
| CN | 102697812 | 10/2012 |
| CN | 104531867 | 4/2015 |

(Continued)

OTHER PUBLICATIONS

Genbank Accession No. EU143239—Clostridium perfringens necrotic enteritis toxin B precursor (netB) gene, complete cds (submitted on Sep. 7, 2007, retrieved on May 12, 2021 from https://www.ncbi.nlm.nih.gov/nuccore/EU143239). (Year: 2007).*

Genbank Accession No. JF298802—Clostridium perfringens strain CPB228 alpha toxin gene, partial cds (submitted on Jan. 30, 2011, retrieved on May 13, 2021 from https://www.ncbi.nlm.nih.gov/nuccore/JF298802). (Year: 2011).*

Genbank Accession No. EU839779—Clostridium perfringens strain S01 phospholipase C (plc) gene, complete cds (submitted Jun. 20, 2008, retrieved on May 13, 2021 from https://www.ncbi.nlm.nih.gov/nuccore/EU839779). (Year: 2008).*

Abildgaard, L., Engberg, R.M., Pedersen, K., Schramm, A. and Hojberg, O., 2009. Sequence variation in the α-toxin encoding plc gene of Clostridium perfringens strains isolated from diseased and healthy chickens. Veterinary microbiology, 136(3-4), pp. 293-299. (Year: 2009).*

(Continued)

*Primary Examiner* — Samuel C Woolwine
*Assistant Examiner* — Olayinka A Oyeyemi
(74) *Attorney, Agent, or Firm* — Law Office of Michael A. Sanzo, LLC

(57) ABSTRACT

The present invention relates to a method for detecting *C. perfringens* induced diseases in animals, the method comprising: a) collecting sample material of a specific animal or of a specific group of animals at consecutive points in time; b) determining the amount of a first marker and a second marker contained in the sample material; and c) determining the ratio of the first marker to the second marker contained in the sample material; wherein the first marker comprises a polynucleotide sequence being specific for the *C. perfringens* sub-species inducing the targeted disease; and the second marker comprises a polynucleotide being specific for the species *C. perfringens*; and wherein an increase in the ratio of the first marker to the second marker in the analyzed sample material over time is an indication of the targeted disease.

19 Claims, No Drawings
Specification includes a Sequence Listing.

(56) References Cited

U.S. PATENT DOCUMENTS

| | | |
|---|---|---|
| 2020/0239938 A1 | 7/2020 | Kappel et al. |
| 2021/0003592 A1 | 1/2021 | Flügel et al. |
| 2021/0011027 A1 | 1/2021 | Flügel et al. |
| 2021/0207193 A1 | 7/2021 | Thiemann et al. |
| 2021/0262031 A1* | 8/2021 | Igwe ................... C12Q 1/689 |

FOREIGN PATENT DOCUMENTS

| | | | |
|---|---|---|---|
| CN | 107090518 | | 8/2017 |
| EP | 2 495 025 | A1 | 9/2012 |
| EP | 2 740 536 | A2 | 6/2014 |
| JP | 2015-039320 | | 3/2015 |
| KR | 2008-0082370 | | 9/2008 |
| RU | 2472162 | | 1/2013 |
| WO | WO 2005/016962 | | 2/2005 |
| WO | WO 2005/122790 | | 12/2005 |
| WO | WO 2008/148166 | | 12/2008 |
| WO | WO 2012/017466 | | 2/2012 |
| WO | WO 2014/012168 | | 1/2014 |
| WO | WO 2014/107571 | | 7/2014 |
| WO | WO 2015/103710 | | 7/2015 |
| WO | WO 2016/011258 | | 1/2016 |
| WO | WO-2016142146 | A2 * | 9/2016 .......... C12Q 1/6883 |
| WO | WO 2016/201272 | | 12/2016 |
| WO | WO 2019/166531 | | 9/2019 |
| WO | WO 2019/166534 | | 9/2019 |
| WO | WO 2019/238561 | | 12/2019 |

OTHER PUBLICATIONS

Albini, S., Brodard, I., Jaussi, A., Wollschläger, N., Frey, J., Miserez, R. and Abril, C., 2008. Real-time multiplex PCR assays for reliable detection of Clostridium perfringens toxin genes in animal isolates. Veterinary microbiology, 127(1-2), pp. 179-185. (Year: 2008).*

Farzan, A., Kircanski, J., DeLay, J., Soltes, G., Songer, J.G., Friendship, R. and Prescott, J.F., 2013. An investigation into the association between cpb2-encoding Clostridium perfringens type A and diarrhea in neonatal piglets. Canadian Journal of Veterinary Research, 77(1), pp. 45-53. (Year: 2013).*

Llanco, L.A., Nakano, V., Ferreira, A.J.P. and Avila-Campos, M.J., 2012. Toxinotyping and antimicrobial susceptibility of Clostridium perfringens isolated from broiler chickens with necrotic enteritis. International Journal of Microbiology Research, 4(7), p. 290. (Year: 2012).*

Albini et al., 2008. Real-time multiplex PCR assays for reliable detection of Clostridium perfringens toxin genes in animal isolates. Veterinary microbiology, 127(1-2), pp. 179-185. (Year: 2008).*

Bailey, M., 2013. The development and use of multiplex PCR protocols for the detection of Clostridium perfringens toxin encoding genes cpa, cpb, etx, ia, cpe, netB, and tpeL (Doctoral dissertation). (Year: 2013).*

Merati, R., Temim, S. and Mohamed, A.A.A.F., 2017. Identification and Characterization of Clostridium perfringensIsolated from necrotic Enteritis in Broiler Chickens in Tiaret, Western Algeria. (Year: 2017).*

Mostafa, A.E.D.H., El-ShahatAbdeen, E. and Abou-Hadeed, M.G., 2016. Research Article Multiplex PCR and Detection of netB Gene of Clostridium perfringens from Broilers with Necrotic Enteritis. (Year: 2016).*

Nagpal et al., 2015. Sensitive quantification of Clostridium perfringens in human feces by quantitative real-time PCR targeting alpha-toxin and enterotoxin genes. BMC microbiology, 15(1), pp. 1-12. (Year: 2015).*

Schlegel et al., 2012. Toxin-associated and other genes in Clostridium perfringens type A isolates from bovine clostridial abomasitis (BCA) and jejunal hemorrhage syndrome (JHS). Canadian Journal of Veterinary Research, 76(4), pp. 248-254. (Year: 2012).*

Singh et al., 2018. Molecular detection of Clostridium perfringens toxinotypes, Enteropathogenic *Escherichia coli*, rotavirus and coronavirus in diarrheic fecal samples of neonatal goat kids. Veterinarski arhiv, 88(1), pp. 1-20. (Year: 2018).*

Wei, S., Gutek, A., Lilburn, M. and Yu, Z., 2013. Abundance of pathogens in the gut and litter of broiler chickens as affected by bacitracin and litter management. Veterinary microbiology, 166(3-4), pp. 595-601. (Year: 2013).*

Wu, S.B., Rodgers, N. and Choct, M., 2011. Real-time PCR assay for Clostridium perfringens in broiler chickens in a challenge model of necrotic enteritis. Applied and environmental microbiology, 77(3), pp. 1135-1139. (Year: 2011).*

Yadav et al., 2017. Molecular characterization and antimicrobial resistance profile of Clostridium perfringens type A isolates from humans, animals, fish and their environment. Anaerobe, 47, pp. 120-124. (Year: 2017).*

Yasugi et al., 2015. In vitro cytotoxicity induced by Clostridium perfringens isolate carrying a chromosomal cpe gene is exclusively dependent on sporulation and enterotoxin production. Microbial pathogenesis, 85, pp. 1-10. (Year: 2015).*

Allaart, J.G., de Bruijn, N.D., van Asten, A.J., Fabri, T.H. and Gröne, A., 2012. NetB-producing and beta2-producing Clostridium perfringens associated with subclinical necrotic enteritis in laying hens in the Netherlands. Avian Pathology, 41(6), pp. 541-546. (Year: 2012).*

Erol et al., 2008. Molecular typing of Clostridium perfringens isolated from turkey meat by multiplex PCR. Letters in applied microbiology, 47(1), pp. 31-34. (Year: 2008).*

Petit, L., Gibert, M. and Popoff, M.R., 1999. Clostridium perfringens: toxinotype and genotype. Trends in microbiology, 7(3), pp. 104-110. (Year: 1999).*

Rood, J.I., Adams, V., Lacey, J., Lyras, D., McClane, B.A., Melville, S.B., Moore, R.J., Popoff, M.R., Sarker, M.R., Songer, J.G. and Uzal, F.A., 2018. Expansion of the Clostridium perfringens toxin-based typing scheme. Anaerobe, 53, pp. 5-10. (Year: 2018).*

Uzal et al., 2012. Clostridium perfringens type C and Clostridium difficile co-infection in foals. Veterinary microbiology, 156(3-4), pp. 395-402. (Year: 2012).*

Miller et al., 2010. Bacteriophage therapy for control of necrotic enteritis of broiler chickens experimentally infected with Clostridium perfringens. Avian diseases, 54(1), pp. 33-40. (Year: 2010).*

International Search Report for international application PCT/EP2016/053502 filed Feb. 19, 2016, corresponding to copending U.S. Appl. No. 15/555,531.

Written Opinion of the International Searching Authority for international application PCT/EP2016/053502 filed Feb. 19, 2016, corresponding to copending U.S. Appl. No. 15/555,531.

International Preliminary Report on Patentability for international application PCT/EP2016/053502 filed Feb. 19, 2016, corresponding to copending U.S. Appl. No. 15/555,531.

Aade, et al., "Haematological parameters change in *Gallus gallus domesticus* infected with cestode parasite," *International Multidisciplinary Research Journal* 2(4):13-15 (accepted Apr. 2012).

Benjamini et al., "Controlling the False Discovery Rate: a Practical and Powerful Approach to Multiple Testing," *J.R. Statist. Soc. B*. 57(1):289-300.

Chen, et al., "Microfluidic isolation and transcriptome analysis of serum microvesicles," *Lab on a Chip* 10:505-511 (available online Dec. 2009).

Cheruvanky, et al., "Rapid isolation of urinary exosomal biomarkers using a nanomembrane ultrafiltration concentrator," *Am. J. Physiol. Renal Physiol*. 292(5):F1657-1661 (May 2007).

Chuka, et al., "A Comparison of the haematological and biochemical indices of broiler and red jungle (Hamburgh) fowl (*Gallus gallus domesticus*)," *Discovery Nature* 1(1):15-18 (Oct. 2012).

Clayton, et al., "Analysis of antigen presenting cell derived exosomes, based on immuno-magnetic isolation and flow cytometry," *J. Immunol. Methods* 247:163-174 (Jan. 2001).

Cooper, et al., "Diagnosing clostridial enteric disease in poultry," *Journal of Veterinary Diagnostic Investigation* 25(3):314-327 (2013).

Dinh, et al., "Modulation of microRNAs in two genetically disparate chicken lines showing different necrotic enteritis disease susceptibility," *Vet. Immunol. Immunopathol*. 159:74-82 (May 2014).

Garcia, et al., "Experimental infection of commercial layers using a *Salmonella enterica* serovar Gallinarum strain: Leukogram and serum acute-phase protein concentrations," *Brazillian Journal of Poultry Science* 11:263-270 (Oct.-Dec. 2009).

(56) References Cited

OTHER PUBLICATIONS

Heikinheimo, et al., "Enumeration and Isolation of cpe-Positive *Clostridium perfringens* Spores from Feces," *Journal of Clinical Microbiology* 42(9):3992-3997 (Sep. 2004).
Jiang, et al., "Membrane vesicles of *Clostridium perfringens* type A strains induce innate and adaptive immunity," *International Journal of Medical Microbiology* 304:431-443 (May 2014).
Keyburn, et al., "Association between avian necrotic enteritis and *Clostridium perfringens* strains expressing NetB toxin," *Vet. Res.* 41:21 (accepted Nov. 2009).
Kim, et al., "Noble Polymeric Surface Conjugated with Zwitterionic Moieties and Antibodies for the Isolation of Exosomes from human Serum," *Bioconjug. Chem.* 23:2114-2120 (Oct. 2012).
Koga, et al., "Exosome can prevent RNase from degrading microRNA in feces," *Journal of Gastrointestinal Oncology* 2(4):215-222 (Dec. 2011).
Leep, et al., "Identification of Novel Pathogenicity Loci in *Clostridium perfringens* Strains That Cause Avian Necrotic Enteritis," *PLOS ONE* 5(5):e10795 (May 2010).
Li, et al., "Claudin-containing exosomes in the peripheral circulation of women with ovarian cancer," *BMC Cancer* 9:244 (Jul. 2009).
Mathivanan, et al., "Proteomics Analysis of A33 Immunoaffinity-purfied Exosomes Released from the Human Colon Tumor Cell Line LIM1215 Reveals a Tissue-specific Protein Signature," *Mol. Cell. Proteomics* 9(2):197-208 (Feb. 2010).
McCourt, et al., "Sandwich ELISA detection of *Clostridium perfringens* cells and α-toxin from field cases of necrotic enteritis of poultry," *Veterinary Microbiology* 106:259-264 (2005).
Miranda, et al., "Nucleic acids within urinary exosomes/microvesicles are potential biomarkers for renal disease," *Kidney International* 78:191-199 (published online Apr. 2010).
Nakamura, et al., "Small cytoplasmic RNA (scRNA) gene from *Clostridium perfringens* can replace the gene for the *Bacillus subtilis* scRNA in both growth and sporulation," *Microbiology* 141:2965-2975 (1995).
Nilsson, et al., "Prostate cancer-derived urine exosomes: a novel approach to biomarkers for prostate cancer," *Br. J. Cancer* 100(10):1603-1607 (May 2009).
Obana, et al., "Structural Requirement in *Clostridium perfringens* Collagenase mRNA 5' Leader Sequence for Translation Induction through Small RNA-mRNA Base Pairing," *Journal of Bacteriology* 195(12):2937-2946 (Jun. 2013).
Ohtani, et al., "Identification of a novel locus that regulates expression of toxin genes in *Clostridium perfringens*," *FEMS Microbiology Letters* 209:113-118 (published online Mar. 2002).
Piercy, "Acute Phase Responses to Experimental Salmonellosis in Calves and Colibacillosis in Chickens: Serum Iron and Caeruloplasmin," *J. Comp. Path.* 89(3):309-319 (Jul. 1979).
Saleem, "Identification of biochemical markers for sub-clinical necrotic enteritis in broiler chickens" (In: Necrotic enteritis, disease induction, predisposing factors and novel biochemical markers in broiler chickens. Chapters, PhD thesis); University of Glasgow, UK (2013).
Schorey, et al., "Exosomes and other extracellular vesicles in host-pathogen interactions," *EMBO Reports* 6(1):24-43 (Jan. 2015).
Shao, et al., "Protein typing of circulating microvesicles allows real-time monitoring of glioblastoma therapy," *Nature Medicine* 18(12):1835-1840 (Dec. 2012).
Skog, et al., "Glioblastoma microvesicles transport RNA and proteins that promote tumour growth and provide diagnostic biomarkers," *Nature Cell Biology* 10(12):1470-1476 (Jan.-Dec. 2008).
Staedel, et al., "MicroRNAs and bacterial infection," *Cellular Microbiology* 15(9):1496-1507 (Sep. 2013).
Taylor, et al., "MicroRNA signatures of tumor-derived exosomes as diagnostic biomarkers of ovarian cancer," *Gynecologic Oncology* 110(1):13-21 (Jul. 2008).
Thery, et al., "Isolation and Characterization of Exosomes from Cell Culture Supernatants and Biological Fluids," *Current Protocols in Cell Biology Chapter 3: Unit 3.22.1* (2006).
Wang, et al., "Integrated analysis of microRNA expression and mRNA transcriptome in lungs of avian influenza virus infected broilers," *BMC Genomics* 13:278 (2012).
Wise, et al., "Quantitive Detection of *Clostridium perfringens* in the Broiler Fowl Gastrointestinal Tract by Real-Time PCR," *Applied and Environmental Microbiology* 71(7):3911-3916 (Jul. 2005).
Witwer, et al., "Standardization of sample collection, isolation and analysis methods in extracellular vesicle research," *Journal Extracellular Vesicles* 2:20360 (May 2013).
Wubbolts, et al., "Proteomic and Biochemical Analyses of Human B Cell-derived Exosomes," *J. Biol. Chem.* 278(13):10963-10972 (Mar. 2003).
Restriction Requirement dated Dec. 4, 2018 for copending U.S. Appl. No. 15/555,531.
Response to Restriction Requirement filed Feb. 4, 2019 for copending U.S. Appl. No. 15/555,531.
Amendment to Accompany Response to Restriction Requirement filed Feb. 4, 2019 for copending U.S. Appl. No. 15/555,531.
Non Final Office Action dated Feb. 21, 2019 for copending U.S. Appl. No. 15/555,531.
Amendment and Response to Non Final Office Action filed Jul. 22, 2019 for copending U.S. Appl. No. 15/555,531.
Final Office Action dated Oct. 9, 2019 for copending U.S. Appl. No. 15/555,531.
Agunos, et al., "A Systematic Review Characterizing On-Farm Sources of *Campylobacter* spp. for Broiler Chickens," *Plos One* 9(8):e104905 (Aug. 2014).
Dallal, et al., "Prevalence and antimicrobial resistance profiles of *Salmonella* serotypes, *Campylobacter* and *Yersinia* spp. Isolated from retail chicken and beef, Tehran, Iran," *Food Control* 21:388-392 (2010).
Devriese, et al., "*Pseudomonas aeruginosa* Infection on a Broiler Farm," *Avian Pathology* 4:233-237 (1975).
Ducatelle, et al., "Biomarkers for monitoring intestinal health in poultry: present status and future perspectives," *Vet. Res.* 49:1-9 (May 2018).
Santos, et al., "Pathobiology of *Salmonella*, intestinal microbiota, and the host innate immune response," *Front. Immunol.* 5:1-7 ((May 2014).
Examiner's Answer for copending application U.S. Appl. No. 15/555,531, dated Jul. 30, 2021.
Reply Brief for copending application U.S. Appl. No. 15/555,531, filed Sep. 29, 2021.
U.S. Appl. No. 17/413,548, filed Jun. 12, 2021, Pelzer.
International Search Report for corresponding PCT/EP2018/062090 filed May 9, 2018.
Written Opinion of the International Searching Authority for corresponding PCT/ EP2018/062090 filed May 9, 2018.
International Preliminary Report on Patentability for corresponding PCT/ EP2018/062090 filed May 9, 2018.
Partial European Search Report and Search Opinion for corresponding EP 17 17 0811 filed May 12, 2017.
Gohari, et al., "A Novel Pore-Forming Toxin in Type A *Clostridium perfringens* Is Associated with Both Fatal Canine Hemorrhagic Gastroenteritis and Fatal Foal Necrotizing Enterocolitis," *PLoS One* 10(4):1-27 (Apr. 2015).
Goossens, et al.,"*Clostridium perfringens* strains from bovine enterotoxemia cases are not superior in in vitro production of alpha toxin, perfringolysin O and proteolytic enzymes," *BMC Veterinary Research* 10(32):1-7 (2014).
Hacker, et al., "Pathogenicity islands of virulent bacteria: structure, function and impact on microbial evolution," *Molecular Microbiology* 23(6):1089-1097 (Mar. 1997).
Keyburn, et al., "NetB, a New Toxin That Is Associated with Avian Necrotic Enteritis Caused by *Clostridium perfringens*," *PLoS Pathogens* 4(2):e26 (Feb. 2008).
Keyburn, et al., "Alpha-Toxin of *Clostridium perfringens* Is Not an Essential Virulence Factor in Necrotic Enteritis in Chickens," *Infection and Immunity* 74(11):6496-6500 (Nov. 2006).
Leburn, et al., "Cattle enterotoxaemia and *Clostridium perfringens*: description, diagnosis and prophylaxis," *Veterinary Record* 167(1):13-22 (Jul. 2010).

(56) References Cited

OTHER PUBLICATIONS

Li, et al., "Toxin Plasmids of *Clostridium perfringens*," *Microbiology and Molecular Biology Reviews* 77(2):208-233 (Jun. 2013).
Pardon, et al., "Longitudinal study on morbidity and mortality in white veal calves in Belgium," *BMC Veterinary Research* 8(26):1-15 (2012).
Parreira, et al., "Sequence of Two Plasmids from *Clostridium perfringens* Chicken Necrotic Enteritis Isolates and Comparison with *C. perfringens* Conjugative Plasmids," *PLoS ONE* 7(11):e49753 (Nov. 2012).
Petit, et al., "*Clostridium perfringens*: toxinotype and genotype," *Trends in Microbiology* 7(3):104-110 (Mar. 1999).
Popoff, et al., "Genetic characteristics of toxigenic Clostridia and toxin gene evolution," *Toxicon* 75:63-89 (available online May 2013).
Popoff, et al., "Clostridial pore-forming toxins: Powerful virulence factors," *Anaerobe* 30:220-238 (available online Jun. 2014).
Rood, "Virulence Genes of *Clostridium perfringens*," *Annu. Rev. Microbiol.* 52:333-360 (1998).
Shojadoost, et al., "The successful experimental induction of necrotic enteritis in chickens by *Clostridium perfringens*: a critical review," *Veterinary Research* 43:74 (2012).
Timbermont, et al., "Necrotic enteritis in broilers: an updated review on the pathogenesis," *Avian Pathology* 40(4):341-347 (2011).
Titball, et al., "The *Clostridium perfringens* α-toxin," *Anaerobe* 5:51-64 (1999).
Wade, et al., "The true cost of necrotic enteritis," *World Poultry* 31:16-17 (2015).
Wisnieswski, et al., "The Tcp conjugation system of *Clostridium perfringens*," *Plasmid* 91:28-36 (May 2017).
"*Clostridium perfringens* NetB DNA SEQ ID: 1", XP-002761707, Database accession No. AUJ86218 (Feb. 2009).
"Human PRO nucleotide sequence SEQ ID: 410", XP-002761706, Database accession No. AUZ24794 (Mar. 2009).
"*Clostridium perfringens* strain NE_10 plasmid pNetB-NE10, complete sequence," XP-002761708, Database accession No. JQ655731 (Dec. 2012).
Database WPI, Thomson Scientific, London, GB; XP-002744039; CN 102 697 812 A (Univ. Shandong Agric.), abstract (Oct. 2012).
U.S. Appl. No. 15/555,531, filed Sep. 4, 2017, US 2018-0312905 A1, Nov. 1, 2018, Igwe.
European Search Report and Search Opinion for EP 19 20 9124 completed Mar. 3, 2020; (division of EP 17 17 0811 filed May 12, 2017).
Kukier, et al., "Epidemiological Investigation of Animal Diseases Caused by *Clostridium perfringens* Strains Isolated From Feedingstuffs," *KRMIVA* 52:339-343 (Jan. 2010).
Park, et al., "Characterization of *Clostridium perfringens* isolates obtained from 2010 to 2012 from chickens with necrotic enteritis in Korea," *Poultry Science* 94(6):1158-1164 (Apr. 2015).
Saita, et al., "Pathogenicity markers of *Clostridium* spp. in commercial turkeys," *Italian Journal of Animal Science* 8(4):781-784 (Jan. 2009).
Wei, et al., "Abundance of pathogens in the gut and litter of broiler chickens as affected by bacitracin and litter management," *Veterinary Microbiology* 166(3-4):595-601 (Oct. 2013).
Database accession No. BDE57256; *Clostridium perfringens* netB gene specific forward PCR primer, (Nov. 2016).
Database accession No. EA946288; Sequence 166055 from U.S. Pat. No. 7,374,927; (Aug. 2008).
Database accession No. EA876028; Sequence 95795 from U.S. Pat. No. 7,374,927; (Aug. 2008).
Database accession No. BCL09680; Avena sativa BAD specific multiplex PCR primer; (Mar. 2016).
Database accession No. BCL16835; Avena sativa BAD specific multiplex PCR primer; (Mar. 2016).
Database accession No. HJ900945; Sequence 97404 from U.S. Pat. No. 8,673,560; (Feb. 2015).
Database accession No. AWZ90261; *Clostridium perfringens* detecting PCR primer; (Jul. 2009).
Database accession No. AFB71766; *Campylobacter* sp. PCR primer; (May 2007).
Database accession No. HW832967; A method for simultaneous detection and/or quantification of multiple bacteria; (Oct. 2015).
Database accession No. GS_NUC_ALERT:WO2016201272. 163953; standard, peptide; (Jun. 2015).
Notice of Appeal filed Jan. 18, 2021, for copending U.S. Appl. No. 15/555,531.
Appeal Brief filed Apr. 19, 2021, for copending U.S. Appl. No. 15/555,531.
Yoo, et al., "Molecular Typing and Epidemiological Survey of Prevalence of *Clostridium perfringens* Types by Multiplex PCR," *Journal of Clinical Microbiology* 35(1):228-232 (Jan. 1997).
Amendment & Response to Accompany RCE filed Feb. 10, 2020 for copending U.S. Appl. No. 15/555,531.
Request for Continued Examination filed Feb. 10, 2020 for copending U.S. Appl. No. 15/555,531.
Non Final Office Action dated Apr. 6, 2020 for copending U.S. Appl. No. 15/555,531.
Response to Non Final Office Action filed Aug. 6, 2020 for copending U.S. Appl. No. 15/555,531.
Allaart, et al., "NetB-producing and beta2-producing *Clostridium perfringens* associated with subclinical necrotic enteritis in laying hens in the Netherlands," *Avian Pathology* 41(6):541-546 (2012).
Lovland, et al., "Diagnosing *Clostridium perfringens*-associated necrotic enteritis in broiler flocks by an immunoglobulin G anti-alpha-toxin enzyme-linked immunosorbent assay," *Avian Pathology* 32(5):527-534 (Oct. 2003).
Abnous, et al., "Diets Enriched in Oat Bran or Wheat Bran Temporally and Differentially Alter the Composition of the Fecal Community of Rats," *The Journal of Nutrition* 139(11):2024-2031 (Sep. 2009).
Akbarmehr, "Isolation of *Salmonella* spp. from poultry (ostrich, pigeon and chicken) and detection of their hilA gene by PCR method," *African Journal of Microbiology Research* 4:(24):2678-2681 (Dec. 2010).
Ammar, et al., "Virulence genotypes of clinical *Salmonella* Serovars from broilers in Egypt," *J. Infect. Dev. Ctries.* 10(4):337-346 (Apr. 2016).
Barwick, et al., "Prevalence of *Giardia* spp. and *Cryptosporidium* spp. on dairy farms in southeastern New York state," *Preventive Veterinary medicine* 59(1-2):1-11 (May 2003).
Black, et al., "Experimental *Campylobacter jejuni* Infection in Humans," *The Journal of Infectious Diseases* 157(3):472-479 (Mar. 1988).
Borges, et al., "Detection of virulence-associated genea in *Salmonella* Enteritidia iaolatea from chicken in South of Brazil," *Pesq. Vet. Bras.* 33(12):1416-1422 (Dec. 2013).
Brassard, et al., "Real-time PCR study of infection dynamics of Torque teno sus viruses in naturally infected pigs from nursery to slaughterhouse," *The Veterinary Journal* 197(2):506-508 (Aug. 2013).
Cardona-Castro, et al., "PCR test to detect hilA gene sequences of *Salmonella* spp in blood and feces samples," Abstracts of the General Meeting of the American Society for Microbiology, vol. 102, Section No. 237, Abstract C-267, p. 148 (May 2002).
Chandler-Bostock, et al., "Diversity of group A rotovirus on a UK pig farm," *Verteinary Microbiology* 180(3-4):205-211 (Nov. 2015).
Elder, et al., "Correlation of enterohemorrhagic *Escherichai coli* 0157 prevalence in feces, hides and carcasses of beef cattle during processing," *PNAS* 97(7):2999-3003 (Mar. 2000).
Fernandes Da Costa, et al., "Protection against avian necrotic entertitis after immunisation with NetB genetic or formaldhyde toxoids," *Vaccine* 31:4003-4008 (2013).
Guyard-Nicodème, et al., "Effect of Feed Additives on Productivity and *Campylobacter* spp. Loads in Broilers Reared under Free Range Conditions," *Frontiers in Microbiology* 8(828):1-7 (May 2017).
Haas, et al., "A Quantitative Real-Time PCR Approach for Assessing *Campylobacter jejuni* and *Campylobacter coli* Colonization in Broiler Herds," *Journal of Food Protection* 80(4):604-608 (Apr. 2017).

(56) References Cited

OTHER PUBLICATIONS

Hofshagen, et al., "Toxin Production by Clostridium perfringens Isolated from Broiler Chickens and Capercaillies (*Tetrao urogallus*) with and without Necrotizing Enteritis," *Avian Diseases* 36(4):837-843 (Oct. 1992).

Hong, et al., "Rapid Detection of *Campylobacter coli, C. jejuni*, and *Salmonella enterica* on Poultry Carcasses by Using PCR-Enzyme-Linked Immunosorbent Assay," *Applied and Environmental Microbiology* 69(6):3492-3499 (Jun. 2003).

Kätterer, et al., "The impact of altered managment on long-term agriculture soil carbon stocks—a Swedish case study," *Nutrient Cycling in Agroecosystems* 70(2):179-187 (Oct. 2004).

Lee, et al., "Identification and cloning of two immunogenic *Clostridium perfringes* proteins, elongation factor Tu (EF-Tu) and pyruvate Terredoxin oxidoreductase (PFO) of *C. perfringens,*" *Research in Veterinary Science* 91(3)e80-e86 (Jan. 2011).

Lee, et al., "Immune and anti-oxidant effects of in ovo selenium proteinate on post-hatch experimental avian necrotic enteritis," *Veterinary Parasitology* 206(3):115-122 (Oct. 2014).

Miles, et al., "Spacial Contrasts of Seasonal and Intraflock Broiler Litter Trace Gas Emissions, Physical and Chemical Properties," *J. Environ. Qual.* 177(2):176-187 (Jan. 2011).

Musella, et al., "On the use of posterior predictive probabilities and prediction uncertainty to tailor informative sampling for parasitological surveillance in livestock," *Veterinary Parasitology* 205(1-2):158-168 (Sep. 2014).

Oosterom, et al., "Origin and Prevalence of *Campylobacter jejuni* in Poultry Processing," *Journal of Food Protection* 46(4):339-344 (Apr. 1983).

Pajaniappan, et al., "The *Campylobacter jejuni* cj0414 and cj0415 genes encode a gluconate dehydrogenase that is involved in chicken colonization," Abstract of the General Meeting of the American Society for Microbiology, vol. 105, p. 30 (2005); General Meeting of the American Society for Microbiology; Atlanta, Jun. 9, 2005).

Perko-Mäkelä, et al., "Distribution of *Campylobacter jejuni* isolates from Turkey Farms and Different Stages at Slaughter Using Pulsed-Field Gel Electrophoresis and flaA-Short Variable Region," *Zoonoses Public Health* 58(6):388-398 (Sep. 2011).

Perko-Mäkelä, et al., "A longitudinal study of *Campylobacter* distribution in a turkey production chain," *Acta Veterinaria Scandinavica* 51(18):1-10 (Apr. 2009).

Schallegger, et al., "Combined *Campylobacter jejuni* and *Campylobacter coli* Rapid Testing and Molecular Epidemiology in Conventional Broiler Flocks," *Zoonoses Public Health* 63(8):588-599 (Dec. 2016).

Schepers, et al., "Site-Specific Considerations for Managing Phosphorus," *J. Environ. Qual.* 29(1):125-130 (Jan. 2000).

Smith, et al., "Phenotypic and genotypic profiling of antimicrobial resistance in enteric *Escherichia coli* communities isolated from finisher pigs in Australia," *Australian Veterinary Journal* 94(10):371-376 (Oct. 2016).

Sun, et al., "Identification and molecular subtyping of *Campylobacter jejuni* isolated from chicken carcass," *Journal of Hygiene Research* 43(4):608-613 (Jul. 2014).

Van De Poel, et al., "Norwalk-Like Calicvirus Genes in Farm Animals," *Research* 6(1)36-43 (Jan.-Feb. 2000).

Whittington, et al., "Use of Pooled Fecal Culture for Sensitive and Economic Detection of *Mycobacterium avium* subsp. *paratuberculosis* Infection in Flocks of Sheep," *Journal of Clinical Microbiology* 38(7):2550-2556 (Jul. 2000).

Williams, et al., "A new method for the experimental production of necrotic enteritis and its use for studies on the relationships between necrotic enteritis, coccidiosis and anticoccidial vaccination of chickens," *Parasitol Res.* 90:19-26 (2003).

Wu, et al., "Optimized Necrotic Enteritis Model Producing Clinical and Subclinical Infection of *Clostridium perfringes* in Broiler Chickens," *Avian Diseases* 54:1058-1065 (2010).

Wu, et al., "Two necrotic enteritis predisposing factors, dietary fishmeal and eimeria infection, induce large change in the caecal microbiota of broiler chickens," *Veterinary Microbiology* 169:188-197 (2014).

Xie, et al., "Prevalence of lapine rotavirus, astrovirus, and hepatitus E virus in Canadian domestic rabbit populations," *Veterinary Microbiology* 208:146-149 (Jul. 2017).

Zhu, et al., "Prevalence and quantification of *Campylobacter* contamination on raw chicken carcasses for retail in China," *Food Control* 75:196-202 (Dec. 2016).

U.S. Appl. No. 16/652,657, filed Mar. 31, 2020, US 2020/0239938 A1, Jul. 30, 2020, Kappel.

U.S. Appl. No. 17/059,431, filed Nov. 28, 2020, Thiemann.

U.S. Appl. No. 17/252,254, filed Dec. 14, 2020, Igwe.

International Search Report for international application PCT/EP2019/054939 filed Feb. 28, 2019, corresponding to copending U.S. Appl. No. 16/977,003.

Written Opinion of the International Searching Authority for international application PCT/EP2019/054939 filed Feb. 28, 2019, corresponding to copending U.S. Appl. No. 16/977,003.

International Preliminary Report on Patentability for international application PCT/EP2019/054939 filed Feb. 28, 2019, corresponding to copending U.S. Appl. No. 16/977,003.

International Search Report for international application PCT/EP2019/054947 filed Feb. 28, 2019, corresponding to copending U.S. Appl. No. 16/977,023.

Written Opinion of the International Searching Authority for international application PCT/EP2019/054947 filed Feb. 28, 2019, corresponding to copending U.S. Appl. No. 16/977,023.

International Preliminary Report on Patentability for international application PCT/EP2019/054947 filed Feb. 28, 2019, corresponding to copending U.S. Appl. No. 16/977,023.

European Search Report and Search Opinion for EP 18159632 filed Mar. 2, 2018, corresponding to international applications PCT/EP2019/054939 and PCT/EP2019/054947.

Abeyrathne, et al., "Sequential separation of lysozyme, ovomucin, ovotransferrin, and ovalbumin from egg white," *Poultry Science* 93(4):1001-1009 (Mar. 2014).

Bischoff, et al., "Intestinal permeability—a new target for disease prevention and therapy," *BMC Gastroenterology* 14(1):189; pp. 1-25 (Nov. 2014).

Chapman, "Milestones in avian coccidiosis research: A review," *Poultry Science* 93:501-511 (2014).

Chen, et al., "Identification of potential biomarkers for gut barrier failure in broiler chickens," *Frontiers in Veterinary Science* 2:14; pp. 1-10 (May 2015).

Dalloul, et al., "Poultry coccidiosis: recent advancements in control measures and vaccine development," *Expert Rev. Vaccines* 5:143-163 (2006).

Ding, et al., "Transport of Antihypertensive Peptide RVPSL, Ovotransferrin 328-332, in Human Intestinal Caco-2 Cell Monolayers," *Journal of Agriculture and Food Chemistry* 63(37):8143-8150 (Sep. 2015).

Fukui, et al., "Changes of Intestinal Functions in Liver Cirrhosis," *Inflammatory Intestinal Diseases* 1(1):24-40 (Published online Mar. 2016).

Gholamiandehkordi, et al., "Quantification of gut lesions in a subclinical necrotic enteritis model," *Avian Pathology* 36(5):375-382 (Oct. 2007).

Gilani, et al., "New biomarkers for increased intestinal permeability induced by dextran sodium sulphate and fasting in chickens," *J Anim Physiol Anim Nutr* 101(5):e237-e245 (2017).

Goossens, et al., "Elevated faecal ovotransferrin concentrations are indicative for intestinal barrier failure in broiler chickens," *Vet Res* 49(1):1-8 (Jun. 2018).

Guerrant, et al., "Biomarkers of Environmental Enteropathy, Inflammation, Stunting and Impaired Growth in Children in Northeast Brazil," *PLOS ONE* 11(9):1-20 (Sep. 2016).

Johnson, et al., "Anticoccidial drugs: lesion scoring techniques in battery and floor-pen experiments with chickens," *Exp Parasitol* 28:30-36 (1970).

Kogut, et al., "Editorial: Gut Health: The New Paradigm in Food Animal Production," *Frontiers in Veterinary Science* 3(71):1-4 (Aug. 2016).

Lee, et al., "Therapeutic potential of hen egg white peptides for the treatment of intestinal inflammation," *Journal of Functional Foods* 1(2):161-169 (Apr. 2009).

(56) References Cited

OTHER PUBLICATIONS

Moore, et al., "Necrotic enteritis predisposing factors in broiler chickens," *Avian Pathology* 45:275-281 (Accepted Jan. 2016).

M'Sadeq, et al., "Towards the control of necrotic enteritis in broiler chickens with in-feed antibiotics phasing-out worldwide," *Animal Nutrition* 1:1-11 (Available online Mar. 2015).

O'Reilly, et al., "Acute phase proteins: a review of their function, behaviour and measurement in chickens," *World Poultry Science Journal* 70(1):27-44 (Mar. 2014).

O'Reilly, Emily "Acute phase proteins and biomarkers for health in chickens," PhD thesis, University of Glasgow, Scotland, pp. 1-137 (Jan. 2016).

O'Reilly, Emily "Acute phase proteins and biomarkers for health in chickens," PhD thesis, University of Glasgow, Scotland, pp. 138-316 (Jan. 2016).

Pavia, et al., "Necrotic enteritis: Applications for the poultry industry," *Journal of Applied Poultry Research* 23:557-566 (2014).

Vicuña, et al., "Dose titration of FITC-D for optimal measurement of enteric inflammation in broiler chicks," *Poultry Science* 94:1353-1359 (Accepted Feb. 2015).

Williams, "Intercurrent coccidiosis and necrotic enteritis of chickens: rational, integrated disease management by maintenance of gut integrity," *Avian Pathology* 34(3):159-180 (2005).

Xie, et al., "Changes in Serum Ovotransferrin Levels in Chickens with Experimentally Induced Inflammation and Diseases," *Avian Dis* 46(1):122-131 (2002).

Final Office Action for copending U.S. Appl. No. 15/555,531, dated Aug. 21, 2020.

U.S. Appl. No. 16/977,003, Flügel.

U.S. Appl. No. 16/977,023, Flügel.

Rahman, et al., "Intestinal Hypoperfusion Contributes to Gut Barrier Failure in Severe Acute Pancreatitis," *J. Gastrointest. Surg.* 7(1):26-36 (2003).

Wu, et al., "Ovotransferrin: Structure, bioactivities and preparation," *Food Research International* 46(2):480-487 (2012).

Decision on Appeal for copending U.S. Appl. No. 15/555,531, dated Dec. 22, 2022.

Amendment & Response to Appeal Decision for copending U.S. Appl. No. 15/555,531, filed Feb. 8, 2023.

Declaration to Accompany Response for copending U.S. Appl. No. 15/555,531, filed Feb. 8, 2023.

\* cited by examiner

SEQUENCE LISTING

<160> NUMBER OF SEQ ID NOS: 16

<210> SEQ ID NO 1
<211> LENGTH: 969
<212> TYPE: DNA
<213> ORGANISM: Clostridium perfringens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (391)..(396)
<223> OTHER INFORMATION: n is a, c, g, or t
<220> FEATURE:
<221> NAME/KEY: misc_feature
<222> LOCATION: (418)..(420)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t

<400> SEQUENCE: 1

```
ttgaaaagan taaaaattat ttcaattaca ctagttctta caagtgtaat tagtacaagc      60
cttttttcaa ctcaaactca gtttttgca agtgaattaa atgacataaa caaaattgag     120
ttgaaaaatc taagtggaga ataataaaa gaaatggaa aggaagctat taaatatact     180
tctagtgata ccgcttcaca taaaggttgg aaggcaactt taagtggaac atttattgaa     240
gatcctcatt ctgataagaa aactgcttta ttaaatttag aaggatttat accttctgat     300
aaacagattt ttggttctaa atattacgga aaaatgaaat ggcctgaaac ttatagaatt     360
aatgtaaaaa gtgctgatgt aaataataat nnnnnnatag caaattctat tcctaaannn     420
actatagata aaaaagatgt atntaattca attggttatt ctataggcgg taatatatct     480
gttgaaggaa aaactgntgg tnctggaata aatgcttcat ataatgtcca aaatactata     540
agctatgaac aacctgattt tagaacaatt caaagaaaag atgatgcaaa tttagcatca     600
tgggatataa aatttgttga gactaaggac ggttataata tagattctta tcatgctatt     660
tatggaaatc aattattcat gaaatcaaga ttgtataata atggtgataa aaatttcaca     720
gatgatagag atttatcaac attaatttct ggtggatttt cacccaatat ggctttagca     780
ttaacagcac ctaaaaatgc taaagaatct gtaataatag ttgaatatca aagatttgat     840
aatgactata ttttaaattg ggaaactact caatggcgag gaacaaacaa actttcgtca     900
acaagtgaat ataacgaatt tatgttttaa ataaattggc aagatcataa aatagaatat     960
tatctgtaa                                                             969
```

<210> SEQ ID NO 2
<211> LENGTH: 1197
<212> TYPE: DNA
<213> ORGANISM: Clostridium perfringens
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature

```
<222> LOCATION: (23)..(24)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
```

```
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (604)..(605)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
```

-continued

```
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (741)..(742)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (825)..(826)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1014)..(1014)
```

```
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1094)..(1094)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1124)..(1124)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t

<400> SEQUENCE: 2
atgaaaagaa agatttgtaa ngnncttntt tgtgcnncgn tagnaactag cctatgggct      60
gggnnatcaa ctaaagtnta ngcttgggat ggaaanattg anggaacagg aactcatgct     120
atgattgnaa ctcaaggnnt ttcaatntta gaaaatgatn tgtcnanaan tgaaccagaa     180
agtgtaagaa aaacttaga gattttaaaa ganaacatgc atgancttca attaggttct     240
acttatccag attatgataa gaangcntat gatntatatc aagatcantt ctgggatcct     300
gatacanata ataatttntc aaaggataat agttggtatt tagcttattc tatacctgan     360
acaggggaat cacaaataag aaaattttca gcnttagcta gatatgaatg caaagaggn     420 aantataanc aagctacatt ctatcttgga gangctatgc actattttgg agatatagat     480
actccatatc atcctgctaa tgttactgcn gttgatagcg caggacatgt taagtttgan     540
acttttgcag angaaagnaa agaacantat aaaataaaca cagnaggttg caaaactaan     600
gagnnttttt atnctgatat nttaaaaaac aangatttta atgcatggtc aaaagaatat     660
gcaagaggtt ttgctaaaan aggnaaatca atatactata gtcatgctag catgagtcat     720
agttgggatg attggganta nncagcaaag gtaactntng ctaactctca aaaaggaaca     780
gcnggatata tttatagatt cttacangat gtatcagagg gtaannatcc atcagttggn     840
aanaatgtaa agaactagt agcttacata tcaactagtg gtganaaaga tgctggaaca     900
gatgactaca tgtattttgg aatcaaaaca aaggatggaa aaactcaaga atgggaaatg     960
ganaacccag gaaatgantt tatgnctgga agnaaagana cttatacttt caanttaaan    1020
gatgaaaatc taaaaattga tgatatacaa aatatgtgga ttagaaaaag aaaatataca    1080
gcattcncag atgnttataa gccagaaaac ataagntaa tagnaaatgg aaaagttgta    1140
gtngacaang atataaanga gtggatttca ggaaattcaa cttataatat aaaataa       1197

<210> SEQ ID NO 3
<211> LENGTH: 20
```

-continued

```
<212> TYPE: DNA
<213> ORGANISM: Artificial Sequence
<220> FEATURE:
<223> OTHER INFORMATION: Primer

<400> SEQUENCE: 3
tatacttcta gtgataccgc                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
atcagaatga ggatcttcaa                                               20

<210> SEQ ID NO 5
<211> LENGTH: 23
<212> TYPE: DNA
<213> ORGANISM: Artificial Sequence
<220> FEATURE:
<223> OTHER INFORMATION: Probe

<400> SEQUENCE: 5
tcacataaag gttggaaggc aac                                           23

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tacatatcaa ctagtggtga                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
attcttgagt ttttccatcc                                               20

<210> SEQ ID NO 8
<211> LENGTH: 27
<212> TYPE: DNA
<213> ORGANISM: Artificial Sequence
<220> FEATURE:
<223> OTHER INFORMATION: Probe

<400> SEQUENCE: 8
tggaacagat gactacatgt attttgg                                       27

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
```

```
agtctacgct tgggatggaa                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tttcctgggt tgttcatttc                                              20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tgataccgct tcacataaag gt                                           22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
accgtcctta gtctcaacaa at                                           22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gttgatagcg caggacatgt taag                                         24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
catgtagtca tctgttccag catc                                         24

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
tcaattggtt attctatagg cggta                                        25

<210> SEQ ID NO 16
<211> LENGTH: 25
<212> TYPE: DNA
<213> ORGANISM: Artificial Sequence
```

```
<220> FEATURE:
<223> OTHER INFORMATION: Primer

<400> SEQUENCE: 16
atatgaagca tttattccag cacca                                              25
```

METHOD FOR DETECTING C. PERFRINGENS INDUCED DISEASES IN ANIMALS

CROSS REFERENCE TO RELATED APPLICATIONS

The present application is US national stage of international application PCT/EP2018/062090, which had an international filing date of May 9, 2018, and which was published on Nov. 15, 2018. The PCT application claims the benefit of U.S. 62/531,000, filed on Jul. 11, 2017. The PCT application also claims priority to European application EP 17170811.8, filed on May 12, 2017 and to Chinese application CN 201710646838.1, filed on Aug. 1, 2017. The contents of each priority application is hereby incorporated by reference herein in its entirety.

SEQUENCE LISTING

The instant application contains a Sequence Listing which has been submitted in ASCII format via EFS-Web. The Sequence Listing was created on Nov. 9, 2019, is named Sequence-Listing-t and is 12,000 bytes in size. This Sequence Listing is hereby incorporated by reference in its entirety.

FIELD OF THE INVENTION

The present invention relates to a method for detecting *C. perfringens* induced diseases in animals. More specifically, the present invention pertains to a method for determining whether or not an animal or an animal population suffers from *C. perfringens* induced diseases in clinical or subclinical state.

BACKGROUND OF THE INVENTION

*Clostridium perfringens* is an ubiquitous pathogen that uses an arsenal of toxins to cause histotoxic and intestinal infections in animals and also in humans. *C. perfringens* is a Gram-positive, rod-shaped, spore forming, oxygen-tolerant anaerobe. Not all *C. perfringens* strains are virulent. The virulent *C. perfringens* strains are traditionally classified into five toxin types (A, B, C, D and E), based on the production of four suspected major toxins (alpha, beta, epsilon and iota). Depending on the toxins produced (major and additional toxins like NetB, Cpb2 and others), the *C. perfringens* sub-species specific syndromes/diseases can be induced in different host organisms [Rood, J. I. (1998) "Virulence genes of *Clostridium perfringens*"; Annual Review of Microbiology 52: 333-360]. The toxins are encoded by polynucleotide sequences located on the chromosome and/or on toxin plasmids [Popoff, M. R. and P. Bouvet (2013). "Genetic characteristics of toxigenic Clostridia and toxin gene evolution" Toxicon 75: 63-89].

As an animal pathogen, *C. perfringens* is responsible for several serious diseases including avian necrotic enteritis, which drains approximately US$6 billion/year from the global agricultural system [Wade, B., Keyburn, A. L. (2015), "The true cost of necrotic enteritis" World Poultry 31, 16-17].

Necrotic enteritis (NE) is an enteric disease of poultry that was first described in 1961. NE in chickens manifests as an acute or chronic enterotoxaemia. The acute disease results in significant levels of mortality due to the development of necrotic lesions in the gut wall, whereas the chronic disease leads to a significant loss of productivity and welfare. Early studies on NE suggested that the main virulence factor involved in the disease was the alpha-toxin (known as Cpa or Plc), which has phospholipase C and sphingomyelinase activity [Keyburn, A. L. et al. (2006) "Alpha-toxin of *Clostridium perfringens* is not an essential virulence factor in necrotic enteritis in chickens", Infection and Immunity 74(11): 6496-6500]. All *C. perfringens* strains harbor the gene encoding the alpha toxin [Rood, J. I. (1998) "Virulence genes of *Clostridium perfringens*", Annual Review of Microbiology 52: 333-360; Titball, R. W., et al. (1999) "The *Clostridium perfringens* α-toxin." Anaerobe 5(2): 51-64]. Recent studies however showed that alpha-toxin seems not to be an essential virulence factor since alpha toxin mutant strains were capable of causing NE, which questions the role of alpha-toxin in the disease in general. In more recent studies, the novel pore forming toxin, NetB, has been suggested to play a major key role in the development of this disease [Keyburn, A. L. et al. (2008) "NetB, a new toxin that is associated with avian necrotic enteritis caused by *Clostridium perfringens*" PLoS Pathogens 4(2)].

NE is known to affect broilers, laying hens, turkeys, and quail. The clinical form is most commonly seen in two to five week-old broilers. Typically, this is also near the time that diets are switched from starter feed to grower feed and near the transition period from the maternal immune system to the adaptive immune system, respectively, so opportunistic *C. perfringens* may take advantage of this transitional period in the intestinal environment and proliferate [Timbermont, L. et al. (2011) "Necrotic enteritis in broilers: An updated review on the pathogenesis." Avian Pathology 40(4): 341-347].

Apart from the mere association of the virulence factors per se to the incidence of NE, there is still a great burden to show the mechanistic link between these factors to the establishment of the disease in birds or of other *C. perfringens* induced diseases in other (farm) animals.

Moreover, relating subclinical NE infection to any of these virulence factors is extremely difficult to achieve since birds are void of signs to warrant their examination earlier before slaughter. Therefore the need for a method for early detection of NE, and most importantly, the subclinical forms of NE, remains imperative. Similar considerations apply for other *C. perfringens* induced diseases of animals, in particular of animals in life stock production such as enteritis in pigs, horses, foals, goats, rabbits, lambs, dogs and cattle; diarrhea in pigs; enterotoxaemia in sheep, goat and cattle; necrotizing enteritis in piglets, lambs, foals and calves (neonatal); typhlocolitis in horse; fatal canine hemorrhagic gastroenteritis; fatal foal necrotizing enterocolitis; gas gangrene (clostridial myonecrosis) in sheep, cattle, horses and other species [Rood, J. I. (1998) "Virulence genes of *Clostridium perfringens*" Annual Review of Microbiology 52: 333-360].

Bovine enterotoxaemia caused by *Clostridium perfringens* is a sudden death syndrome with necro-hemorrhagic lesions in the small intestine, which mainly affects suckling calves and veal calves [Goossens, E. et al. (2014), "*Clostridium perfringens* strains from bovine enterotoxaemia cases are not superior in in vitro production of alpha toxin, perfringolysin O and proteolytic enzymes" BMC Veterinary Research 10; Lebrun M, Mainil J G, Linden A: "Cattle enterotoxaemia and *Clostridium perfringens*: description, diagnosis and prophylaxis" Vet Rec 2010, 167 (1):13-22]. In veal calves, predominantly beef cattle breeds are affected. The syndrome accounts for approximately 20% of the mortalities in these calves, compared to 4% in dairy and mixed breed veal calves [Pardon B, De Bleecker K, Hostens M, Callens J, Dewulf J, Deprez P: "Longitudinal study on morbidity and mortality in white veal calves in Belgium" *BMC Vet Res* 2012, 8:26].

Current methods are based on the examination of individualized animals and make use of necropsy and subsequent histopathology or tests to identify the pathogen. However, monitoring of tissue biomarkers or blood biomarkers is, because of its invasive nature, time-consuming and impractical, when large numbers of samples are involved like for farm animals.

Recently published European Patent Application EP 3 112 474 A1 describes a method for detecting avian NE by isolating microvesicles from an avian sample and subsequently determining the presence and/or the level of RNA markers indicative for NE. The avian sample may be a bodily fluid or a bodily excrement and the marker indicative for NE is selected from specific *C. perfringens* and host sequences, homologues and fragments thereof. However, the microvesicles have to be isolated and lysed prior to analysis and quantification of the RNA markers.

It was thus a remaining need to provide a fast and reliable, non-invasive ante mortem method for determining whether or not an animal population suffers from diseases induced by *C. perfringens* that can be performed at low cost and with minimal effort.

SUMMARY OF THE INVENTION

Accordingly, one object of the present invention is to provide a method for detecting *C. perfringens* induced diseases in animals, the method comprising:
  a) collecting sample material of a specific animal or of a specific group of animals at consecutive points in time;
  b) determining the amount of a first marker and a second marker contained in the sample material; and
  c) determining the ratio of the first marker to the second marker contained in the sample material;
  wherein the first marker comprises a polynucleotide sequence being specific for the *C. perfringens* sub-species inducing the targeted disease;
  and the second marker comprises a polynucleotide being specific for the species *C. perfringens*; and
  wherein an increase in the ratio of the first marker to the second marker in the analyzed sample material over time is an indication of the targeted disease.

A further objective of the present invention is the provision of a diagnostic kit comprising PCR primers and probes for both, the first marker and the second marker.

In addition, the present invention provides a method for detecting avian necrotic enteritis, the method comprising
  a) collecting sample material of a specific avian or of a specific group of avians at consecutive points in time;
  b) determining the amount of a first marker and a second marker contained in the sample material; and
  c) determining the ratio of the first marker to the second marker contained in the sample material;
  wherein the first marker is netB and the second marker is cpa;
  and
  wherein an increase in the ratio of the first marker to the second marker in the analyzed sample material over time is an indication of avian necrotic enteritis.

Moreover, the present invention provides an additional method for detecting avian necrotic enteritis, the method comprising
  a) collecting excremental samples of a specific avian or of a specific avian population at consecutive points in time; and
  b) monitoring the level of marker gene netB in these samples;
  wherein an increase in the level of netB constitutes an indication of avian necrotic enteritis.

Finally, the present invention pertains to a method for determining the grade of avian necrotic enteritis, the method comprising
  a) collecting excremental samples of a specific avian or of a specific avian population; and
  b) determining the amount of netB marker gene in these avian excremental samples, wherein the amount of netB marker gene indicates the grade of necrotic enteritis.

In the following, the crucial aspects of the present invention are described in detail.

DETAILED DESCRIPTION OF THE INVENTION

Detection of *C. perfringens* Induced Diseases in Animals

The present inventors have unexpectedly found that the ratio of a first marker polynucleotide to a second marker polynucleotide in animal excrements correlates with the manifestation of diseases being induced by the bacterium *C. perfringens*. More specifically, the present inventors have found that an increase in the ratio of the above-mentioned markers over time is an indication of the targeted disease.

Accordingly, the present invention pertains to a method for detecting *C. perfringens* induced diseases in animals, the method comprising:
  a) collecting sample material of a specific animal or of a specific group of animals at consecutive points in time;
  b) determining the amount of a first marker and a second marker contained in the sample material; and
  c) determining the ratio of the first marker to the second marker contained in the sample material;
  wherein the first marker comprises a polynucleotide sequence being specific for the *C. perfringens* sub-species inducing the targeted disease;
  and the second marker comprises a polynucleotide being specific for the species *C. perfringens*; and
  wherein an increase in the ratio of the first marker to the second marker in the analyzed sample material over time is an indication of the targeted disease.

As used herein, the term "polynucleotides" refers to DNA or RNA. In a particularly preferred embodiment, the term "polynucleotides" refers to DNA.

As used herein, the term "disease" refers to any abnormal condition in an animal that interferes with its vital physiological processes, caused by pathogenic *C. perfringens* strains. The term "disease" corresponds to an increase of pathogenicity factors and thus also includes early stages of the targeted disease as well as a certain risk that the targeted disease will break out. In accordance therewith and as used in the context of the present invention, the term "targeted disease" refers to the specific *C. perfringens* induced disease (occurring in specific animal species) for which the animal sample is to be analyzed.

Markers

The first marker comprises a polynucleotide sequence being specific for the *C. perfringens* sub-species inducing the targeted disease. That is, the first marker represents a specific and conserved region determining the virulence and pathogenicity of the selected *C. perfringens* sub-species. In a preferred embodiment, the first marker constitutes a virulence factor for the targeted disease.

The first marker may be either a marker gene encoding a specific toxin or homologues or fragments thereof, or, alternatively, a pathogenicity island. In the context of the present invention, the term "homologue" refers to a polynucleotide sequence having a sequence identity of at least 80%, preferably at least 85, 90 or 95%, most preferably 100%, to the respective polynucleotide or marker gene. The term "fragment" refers to a polynucleotide sequence being truncated by not more than 100 or 80, preferably by not more than 70, The main diseases associated with *C. perfringens* in animals and the key toxins are listed in the following table [Popoff, M. R. (2014) "Clostridial pore-forming toxins: Powerful virulence factors." *Anaerobe* 30: 220-238; Rood, J. I. (1998) "Virulence genes of *Clostridium perfringens*" *Annual Review of Microbiology* 52: 333-360; Gohari, I. M. et al. (2015) "A novel pore-forming toxin in type A *Clostridium perfringens* is associated with both fatal canine hemorrhagic gastroenteritis and fatal foal necrotizing enterocolitis" *PLoS ONE* 10(4); Keyburn, A. L., et al. (2008) "NetB, a new toxin that is associated with avian necrotic enteritis caused by *Clostridium perfringens*" *PLoS Pathogens* 4(2)]:

| Disease | Host | Virulence factor | Reference |
| --- | --- | --- | --- |
| gas gangrene (clostridial myonecrosis) | Human | Perfringolysin (Theta-Toxin), Alpha toxin (Cpa) | Rood, 1998 |
| food poisoning (food borne poisoning), sporadic diarrhea | Human | Enterotoxin (Cpe) | Popoff, 2014 |
| Diarrhea | Pig | Enterotoxin (Cpe) | Popoff, 2014 |
| enteritis necroticans (pigbel; Darmbrand) | Human | Beta-toxin (Cpb) | Rood, 1998 |
| Enterotoxemia | Sheep, goat, cattle | Epsilon toxin (Etx) | Popoff, 2014 |
| Unidentified | Human, animals | Delta toxin | Popoff, 2014 |
| Necrotizing enteritis | Piglet, calve | Beta-toxin (Cpb) | Popoff, 2014 |
| Enterotoxemia (struck) | Sheep | Beta-toxin (Cpb) | Popoff, 2014 |
| Necrotizing enteritis | Piglet | Beta2-toxin (Cpb2) | Popoff, 2014 |
| Typhlocolitis | Horse | Beta2-toxin (Cpb2) | Popoff, 2014 |
| fatal canine hemorrhagic gastroenteritis | Canine | NetF | Gohari, 2015 |
| fatal foal necrotizing enterocolitis | Foal | NetF | Gohari, 2015 |
| avian necrotic enteritis | Avians | NetB | Keyburn, 2008 | especially by not more than 60, most preferably by not more than 50 nucleotides compared to the respective polynucleotide or marker gene.

As used herein, the term "pathogenicity island" (PAI) refers to discrete genetic units carrying genes encoding for one or more virulence factors [Hacker et al. (1997) "Pathogenicity islands of virulent Bacteria: structure and impact on microbial evolution", *Molecular Microbiology* 23(6): 1089-1097]. The PAI may either contain genes to regulate the virulence genes encoded on the PAI or it may contain genes to regulate genes outside of the PAI. Pathogenicity islands are incorporated in the genome (chromosomally or extrachromosomally) of the pathogenic *C. perfringens* strain.

The first marker may be located on a toxin plasmid of *C. perfringens* and/or on the *C. perfringens* chromosome.

As an example, the cpe gene may be used as a first marker gene. Said cpe gene may be found in a variable region on the chromosome in some *C. perfringens* strains and on large plasmids in other strains [Petit et al. (1999) "*Clostridium perfringens*: toxinotype and genotype", *Trends in Microbiology* Vol. 7, No. 3, 104-110].

In a particularly preferred embodiment, the marker gene is located on a toxin plasmid of *C. perfringens*.

*C. perfringens* strains can carry multiple large toxin and antibiotic resistance plasmids, whereby these plasmids are closely related sharing up to 35 kb of almost identical sequences [Wisnieswski et al. (2017) "The Tcp conjugation system of *Clostridium perfringens*", Plasmid 91, 28-36]. Plasmid-encoded toxins are for example the beta-toxin, the beta2-toxin, the epsilon-toxin, the iota-toxin, NetB and TpeL [Li, J., et al. (2013); "Toxin plasmids of *Clostridium perfringens*"; Microbiology and Molecular Biology Reviews 77(2): 208-233].

Accordingly, the first marker gene may also be selected from the group consisting of cpe, beta-toxin (cpb), beta2-toxin (cpb2), epsilon-toxin (etx), netF and netB and homologues and fragments of these genes. Alternatively, polynucleotide sequences comprising one of the aforementioned genes may also be used. Preferably, these polynucleotide sequences are being elongated by not more than 100 base pairs or not more than 80 base pairs, preferably by not more than 70 base pairs or by not more than 60 base pairs, especially by not more than 50 base pairs or not more than 40 base pairs and most preferably by not more than 30 base pairs compared to the respective marker genes.

In a preferred embodiment, the gene netB is used as the first marker.

The second marker comprises a polynucleotide sequence being specific for the species *C. perfringens* in general and represents a conserved and specific region on the *C. perfringens* genome (chromosomally or extrachromosomally).

The second marker may be a polynucleotide sequence or a specific marker gene located on a plasmid of *C. perfringens* or on the *C. perfringens* chromosome. A marker gene located on the *C. perfringens* chromosome is particularly preferred.

Preferably, the second marker gene is selected from the group consisting of the genes cpa, 16S rDNA, virR, virS, pfoA and homologues and fragments of these genes. Alternatively, polynucleotide sequences comprising one of the aforementioned genes may also be used.

The gene cpa is particularly preferred as the second marker.

The *C. perfringens* induced disease may be selected from the group consisting of avian necrotic enteritis; enteritis in dogs, pigs, horses, foals, goats, rabbits, lambs and cattle; diarrhea in pigs; enterotoxemia in sheep, goat and cattle;

necrotizing enteritis in piglets, lambs, foals and calves (neonatal); typhlocolitis in horse; fatal canine hemorrhagic gastroenteritis; fatal foal necrotizing enterocolitis; gas gangrene (clostridial myonecrosis) in sheep, cattle, horses and other spp. or in humans and human enteritis necroticans. The above method is particularly suitable for detecting avian necrotic enteritis.

Moreover, the method according to the present invention is particularly suitable for detecting *C. perfringens* induced diseases being in sub-clinical or latent state. In such sub-clinical or latent forms of the *C. perfringens* infections, no overt clinical signs are present and usually there is no peak mortality. In a particularly preferred embodiment, the above method is used for detecting avian necrotic enteritis is sub-clinical or latent state.

Determination of *C. perfringens* Induced Diseases in Individual Animals

The method of the present invention may be used for determining whether or not an individual animal suffers from a *C. perfringens* induced disease. In that case, the sample material originates from an individual animal.

The individual animal may for example be a pet or domestic animal, a farm animal as occurring in life stocks, a wild-living animal or a zoo animal. Further, animal individuals being transported for slaughter or for re-location may be examined using the above method.

As an example, sample material originating from an individual dog collected at consecutive points in time can be analyzed in accordance with the above method in order to determine whether or not the dog suffers from fatal canine hemorrhagic gastroenteritis. In this specific case, netF is a suitable first marker and cpa is a suitable second marker.

The sample material is selected from the group consisting of dust samples, swab samples, litter samples, liquid manure samples, fur samples, feather samples, skin samples and samples of bodily excrements and solutions or suspensions thereof. Bodily excrements are urine, fecal or cecal excrements. In a preferred embodiment, the sample material is feces.

In general, the term "litter" is to be understood as a mixture of animal excrements with the bedding material.

As used in the context of this embodiment, the term "litter samples" refers to excremental droppings from an individual animal. Further, in the context this embodiment, the term "liquid manure samples" refers to an excremental sample containing feces and urine from an individual animal.

Samples from individual animals can be taken either directly from the animal, e.g. with swabs. Alternatively and especially in case of single-housed animals, the sample material can be collected from the floor of the pen, cage or slat. The sample material has to be assignable to the investigated animal.

Suitable sample volumes are, for example, 0.05 ml to 20 ml or 0.1 to 20 ml, in particular 0.2 to 10 ml, preferably 0.5 to 5 ml. Suitable sample masses are, for example 0.05 g to 20 g or 0.1 to 20 g, in particular 0.2 to 10 g, preferably 0.5 to 5 g.

Determination of *C. perfringens* Induced Diseases in Animal Populations

In an alternative embodiment, the inventive method is used for determining whether or not an animal population suffers from a *C. perfringens* induced disease.

As used herein, the term "animal population" refers to a group of animal individuals belonging to the same species. The animal population may for example be a group of pets or domestic animals as occurring in animal breeding, a group of farm animals as occurring in life stock production or in life stock breeding, or a group of wild-living animals or zoo animals.

In a preferred embodiment, the animal population is an animal flock as occurring in life stock production processes. For example, the animal population or the animal flock can be an avian flock; a flock of sheep, goat or cattle, a flock of horses or a flock of pigs.

The method of the present invention is particularly suitable for determining the health status of an animal population via bulk testing. As used herein, the term "bulk testing" refers to a test method, wherein the sample material is a pooled sample of an animal population. A "pooled sample" is to be understood as a composite sample from randomly selected separate samples, one sample taken with one or several moistened fabric swabs or pooled samples made up of separate samples of fresh samples taken at random from a number of sites in the house or space in which the animal population or the animal flock is kept. The pooled samples reflect the amount of pathogen marker polynucleotides or marker genes present in the animal population.

The sample material is selected from the group consisting of dust samples, litter samples, liquid manure samples, fur samples, feather samples, skin samples, swab samples and samples of bodily excrements and solutions or suspensions thereof. Bodily excrements are urine, fecal or cecal excrements. In a preferred embodiment, the sample material is feces.

As used in the context of this embodiment, the term "litter samples" refers to mixed excremental droppings in the pen cage or slat. Further, in the context this embodiment, the term "liquid manure samples" refers to mixed excremental samples containing feces and urine.

These litter samples can, for example, be collected from an animal population using the overshoe method or using litter grabs at different places in the pen.

Boot swabs being sufficiently absorptive to soak up moisture are particularly suitable for collecting pooled animal samples. Tube gauze socks are also acceptable.

Suitable sample volumes are, for example, 0.1 to 20 ml, in particular 0.2 to 10 ml, preferably 0.5 to 5 ml. Suitable sample masses are, for example 0.1 to 20 g, in particular 0.2 to 10 g, preferably 0.5 to 5 g.

The animal population preferably is an avian flock. The avian flock according to the invention is preferably poultry. Preferred poultry according to the invention are chickens, turkeys, ducks and geese. The poultry can be optimized for producing young stock. This type of poultry is also referred to as parent and grandparent animals. Preferred parent and grandparent animals are, accordingly, (grand)parent broilers, (grand)parent ducks, (grand)parent turkeys and (grand)parent geese.

The poultry according to the invention can also be selected from fancy poultry and wild fowl. Preferred fancy poultry or wild fowl are peacocks, pheasants, partridges, guinea fowl, quails, capercaillies, goose, pigeons and swans. Further preferred poultry according to the invention are ostriches and parrots. Most preferred poultry according to the invention are broilers.

In order to perform the above method, the animal samples are collected in consecutive points in time. Preferably, the samples are taken on a weekly, daily or hourly basis. Collecting the animal samples at consecutive days is particularly preferred.

In a particularly preferred embodiment, the first and the second marker are detected on DNA level, i.e. the polynucleotides are DNA-polynucleotides.

The marker polynucleotides may be isolated from the animal samples prior to quantification. Polynucleotide isolation can, for example, be performed via extraction using the Cetyltrimethylammoniumbromid (CTAB) method or by diverse commercial nucleic acid extraction kits, in which cell lysis is achieved either through chemical lysis and/or by mechanical cell disruption and nucleic acid is captured on silica matrices or on silica-cladded magnetic beads. Commercial extraction kits specialized on fecal material or harsh material are particularly suitable.

The marker genes may be detected and/or quantified by commonly known methods such as sequencing, hybridization or various PCR techniques known in the art.

In an alternative embodiment, the marker genes contained in the animal sample can be directly quantified, for example via PCR, qPCR, sequencing or hybridization techniques.

The present invention further provides a diagnostic kit comprising a set of oligonucleotides (primers and probes) for amplifying and/or quantifying at least one polynucleotide encoding at least one of the marker genes. In a preferred embodiment, the diagnostic kit comprises PCR primers and probes for both, the first marker and the second marker. More specifically, the diagnostic kit comprises PCR primers and probes for detecting both, the first marker and the second marker, wherein the first marker comprises a polynucleotide sequence being specific for the *C. perfringens* sub-species inducing the targeted disease; and the second marker comprises a polynucleotide being specific for the species *C. perfringens*. The kit may further comprise buffer solutions, such as PCR buffer; magnesia salts; deoxy nucleotide triphosphates (dNTPs). The kit may also include elements such as sample collection tubes, reagents to isolate the nucleic acids and/or instructions for its use.

Detection of Avian Necrotic Enteritis

The applicants have unexpectedly found that the occurrence of (sub-clinical) necrotic enteritis can be determined by monitoring the development of the netB/cpa ratio in avian samples over time.

In accordance thereto, the present invention provides a method for detecting avian necrotic enteritis, the method comprising:
a) collecting samples of a specific avian or of a specific avian population at consecutive points in time;
b) determining the amount of a first marker and a second marker contained in the sample material; and
c) determining the ratio of the first marker to the second marker contained in the sample material;
wherein the first marker is netB or homologues or fragments thereof;
the second marker is cpa or homologues or fragments thereof;
and
wherein an increase in the ratio of the first marker to the second marker in the analyzed sample material over time is an indication of avian necrotic enteritis.

As an alternative, the first marker may also be a polynucleotide sequence comprising netB and/or the second marker may be a polynucleotide sequence comprising cpa. Preferably, these polynucleotide sequences are being elongated by not more than 100 base pairs or not more than 80 base pairs, preferably by not more than 70 base pairs or by not more than 60 base pairs, especially by not more than 50 base pairs or not more than 40 base pairs and most preferably by not more than 30 base pairs compared to the genes netB and cpa.

The term "necrotic enteritis" refers to NE both in clinical and in sub-clinical/latent state.

Therefore, in a particularly preferred embodiment, the present invention provides a method for detecting avian necrotic enteritis, the method comprising:
a) collecting samples of a specific avian or of a specific avian population at consecutive points in time;
b) determining the amount of a first marker and a second marker contained in the sample material; and
c) determining the ratio of the first marker to the second marker contained in the sample material;
wherein the first marker is netB and the second marker is cpa;
and
wherein an increase in the ratio of the first marker to the second marker in the analyzed sample material over time is an indication of avian necrotic enteritis.

The polynucleotide sequences of netB and cpa are known in the art. However, for the sake of clarity and completeness, the consensus sequence of netB is indicated under SEQ ID NO. 1 and the consensus sequence of cpa is indicated under SEQ ID NO. 2.

The alpha toxin gene (cpa) is present on the chromosome of all *C. perfringens* strains (pathogenic and non-pathogenic), meaning that the concentration of cpa should have similar levels in excremental samples of healthy and NE-infected animals and indicates the presence of *C. perfringens* only in general.

The above method may be used for determining whether or not an individual avian subject suffers from (sub-clinical/latent) necrotic enteritis, or, in an alternative embodiment, for determining whether or not an avian population suffers from (sub-clinical/latent) necrotic enteritis ("bulk testing").

In case an individual avian subject is to be examined, the sample material may be selected from the group consisting of dust samples, swab samples, litter samples, liquid manure samples, feather samples and samples of bodily excrements and solutions or suspensions thereof. Bodily excrements are urine, fecal or cecal excrements. In a preferred embodiment, the sample material is feces.

In general, the term "litter" is to be understood as a mixture of animal excrements with the bedding material.

As used in the context of this embodiment, the term "litter samples" refers to excremental droppings from an individual avian subject. Further, in the context this embodiment, the term "liquid manure samples" refers to an excremental sample containing feces and urine from an individual animal.

Samples from individual avian subjects can be taken either directly from the avian, e.g. with swabs. Alternatively and especially in case of single-housed avians, the sample material can be collected from the floor of the pen, cage or slat. The sample material has to be assignable to the investigated animal.

Suitable sample volumes are, for example, 0.05 ml to 20 ml or 0.1 to 20 ml, in particular 0.2 to 10 ml, preferably 0.5 to 5 ml. Suitable sample masses are, for example 0.05 g to 20 g or 0.1 to 20 g, in particular 0.2 to 10 g, preferably 0.5 to 5 g.

In case the health status of an avian population is to be determined, a pooled sample of the avian population is examined ("bulk testing"). A "pooled sample" is to be understood as a composite sample from randomly selected separate samples, one sample taken with one or several moistened fabric swabs or pooled samples made up of separate samples of fresh samples taken at random from a number of sites in the house or space in which the avian population is kept. The pooled samples reflect the amount of pathogenic netB marker genes present in the animal population.

The sample material may be selected from the group consisting of dust samples, litter samples, liquid manure samples, feather samples, swab samples and samples of bodily excrements and solutions or suspensions thereof. Bodily excrements are fecal or cecal excrements. In a preferred embodiment, the sample material is feces.

As used in the context of this embodiment, the term "litter samples" refers to mixed excremental droppings in the pen, cage or slat. These litter samples can, for example, be collected from a population using the overshoe method or using litter grabs at different places in the pen. Further, in the context this embodiment, the term "liquid manure samples" refers to mixed excremental samples containing feces and urine.

Boot swabs being sufficiently absorptive to soak up moisture are particularly suitable for collecting pooled avian samples. Tube gauze socks are also acceptable.

The animal population preferably is an avian flock. The avian flock according to the invention is preferably poultry. Preferred poultry according to the invention are chickens, turkeys, ducks and geese. The poultry can be optimized for producing young stock. This type of poultry is also referred to as parent and grandparent animals. Preferred parent and grandparent animals are, accordingly, (grand)parent broilers, (grand)parent ducks, (grand)parent turkeys and (grand) parent geese.

The poultry according to the invention can also be selected from fancy poultry and wild fowl. Preferred fancy poultry or wild fowl are peacocks, pheasants, partridges, guinea fowl, quails, capercaillies, goose, pigeons and swans. Further preferred poultry according to the invention are ostriches and parrots. Most preferred poultry according to the invention are broilers.

Suitable sample volumes are, for example, 0.1 to 20 ml, in particular 0.2 to 10 ml, preferably 0.5 to 5 ml. Suitable sample masses are, for example 0.1 to 20 g, in particular 0.2 to 10 g, preferably 0.5 to 5 g.

The samples are generally to be taken and analyzed on a weekly, daily or hourly basis. In a preferred embodiment, the animal samples are collected at consecutive days. Preferably, sample collection and sample analysis are started before day 14. For example, sample collection and sample analysis is started from day 1, from day 5, from day 10 or from day 13 on a daily basis.

The marker genes netB and cpa may be isolated from the animal samples prior to quantification. Polynucleotide isolation can, for example, be performed via extraction using the Cetyltrimethylammoniumbromid (CTAB) method or by diverse commercial nucleic acid extraction kits, in which cell lysis is achieved either through chemical lysis and/or by mechanical cell disruption and nucleic acid is captured on silica matrices or on silica-cladded magnetic beads. Commercial extraction kits specialized on fecal material or harsh material are particularly suitable.

The marker genes may be detected and/or quantified by commonly known methods such as sequencing, hybridization or various PCR techniques known in the art.

In an alternative embodiment, the marker genes contained in the animal sample can be directly quantified, for example via PCR, qPCR, sequencing or hybridization techniques.

Intestinal lesions caused by sub-clinical or clinical necrotic enteritis were scored using a scale from 0 to 6 [Keyburn et al. (2006) "Alpha toxin of *Clostridium perfringens* is not an essential virulence factor in necrotic enteritis in chickens", Infect. Immun. 74:6496-6500]. In accordance therewith, the lesions in the small intestine (duodenum to ileum) were scored as follows: score 0=no gross lesions; 1=congested intestinal mucosa; 2=small focal necrosis or ulceration (1-5 foci); 3=focal necrosis or ulceration (6-15 foci); 4=focal necrosis or ulceration (16 or more foci); 5=patches of necrosis 2-3 cm long; 6=diffuse necrosis typical of field cases. Lesion scores 5 to 6 correspond to clinical necrotic enteritis; lesion scores 1 to 4 correspond to the sub-clinical state.

The inventors have found that ratio of netB/cpa marker genes in avian excrement samples at a level of 0.5 already show traces of congested intestinal mucosa.

Accordingly, the present invention also provides a method for detecting necrotic enteritis, the method comprising
  a) collecting an avian sample
  b) determining the amount of marker genes netB and cpa in this avian sample, and
  c) determining the ratio of netB/cpa marker genes in the avian samples,
wherein a netB/cpa ratio being greater than 0.5 constitutes an indication of necrotic enteritis.

In addition, the present invention also provides new PCR primers and probes suitable for detecting and/or quantifying the netB and cpa marker genes present in the excrements of animals infected with necrotic enteritis. As used herein, the term "(PCR) probe" refers to an oligonucleotide sequence that increases the specificity of quantitative PCR.

The oligonucleotide primers and probes described in the following turned out to be particularly effective. Accordingly, the present invention provides oligonucleotides selected from the group consisting of
  a) oligonucleotides having a sequence identity of at least 80%, preferably at least 85, 90 or 95%, most preferably 100%, to the polynucleotide as depicted in SEQ ID NO:3;
  b) oligonucleotides having a sequence identity of at least 80%, preferably at least 85, 90 or 95%, most preferably 100%, to the polynucleotide as depicted in SEQ ID NO: 4;
  c) oligonucleotides having a sequence identity of at least 80%, preferably at least 85, 90 or 95%, most preferably 100%, to the polynucleotide as depicted in SEQ ID NO: 5;
  d) oligonucleotides having a sequence identity of at least 80%, preferably at least 85, 90 or 95%, most preferably 100%, to the polynucleotide as depicted in SEQ ID NO: 6;
  e) oligonucleotides having a sequence identity of at least 80%, preferably at least 85, 90 or 95%, most preferably 100%, to the polynucleotide as depicted in SEQ ID NO: 7;
  f) oligonucleotides having a sequence identity of at least 80%, preferably at least 85, 90 or 95%, most preferably 100%, to the polynucleotide as depicted in SEQ ID NO:8;
  g) oligonucleotides being complementary to the oligonucleotides according to (a) to (f)
  h) oligonucleotides comprising any one of the oligonucleotides according to (a) to (g) and being elongated by not more than 5 nucleotides compared to the oligonucleotides according to (a) to (g).

Therein, the polynucleotide as depicted in SEQ ID NO: 3 is a PCR primer (fwd) for detecting netB. The polynucleotide as depicted in SEQ ID NO: 4 is a PCR primer (rev) for detecting netB. The polynucleotide as depicted in SEQ ID NO: 5 is a PCR probe for detecting netB.

Further, the polynucleotide as depicted in SEQ ID NO: 6 is a PCR primer (fwd) for detecting cpa. The polynucleotide as depicted in SEQ ID NO: 7 is a PCR primer (rev) for detecting cpa. The polynucleotide as depicted in SEQ ID NO: 8 is a PCR probe for detecting cpa.

These oligonucleotides are preferably used as primers and/or probes in one of the above-described methods for detecting necrotic enteritis.

Accordingly, the oligonucleotides selected from the group consisting of
a) oligonucleotides having a sequence identity of at least 80%, preferably at least 85, 90 or 95%, most preferably 100%, to the polynucleotide as depicted in SEQ ID NO:3;
b) oligonucleotides having a sequence identity of at least 80%, preferably at least 85, 90 or 95%, most preferably 100%, to the polynucleotide as depicted in SEQ ID NO: 4;
c) oligonucleotides having a sequence identity of at least 80%, preferably at least 85, 90 or 95%, most preferably 100%, to the polynucleotide as depicted in SEQ ID NO: 5;
d) oligonucleotides having a sequence identity of at least 80%, preferably at least 85, 90 or 95%, most preferably 100%, to the polynucleotide as depicted in SEQ ID NO: 6;
e) oligonucleotides having a sequence identity of at least 80%, preferably at least 85, 90 or 95%, most preferably 100%, to the polynucleotide as depicted in SEQ ID NO: 7;
f) oligonucleotides having a sequence identity of at least 80%, preferably at least 85, 90 or 95%, most preferably 100%, to the polynucleotide as depicted in SEQ ID NO:8;
g) oligonucleotides being complementary to the oligonucleotides according to (a) to (f);
h) oligonucleotides comprising any one of the oligonucleotides according to (a) to (g) and being elongated by not more than 5 base pairs compared to the oligonucleotides according to (a) to (g);
are used in the above-described method as a PCR primer and/or as a PCR probe.

The present invention further provides a diagnostic kit for determining whether or not an avian population, such as an avian flock, suffers from (sub-clinical) necrotic enteritis. Said kit comprises a set of oligonucleotides for amplifying and/or quantifying at least one polynucleotide encoding at least one of the marker genes netB and/or cpa. Preferably, the diagnostic kit comprises PCR primers and probes for both, netB and cpa. The kit may comprise one or more oligonucleotides having a sequence identity of at least 80%, preferably at least 85, 90 or 95%, most preferably 100%, to one or more of the polynucleotides as depicted in SEQ ID NO:3, SEQ ID NO:4, SEQ ID NO:5, SEQ ID NO:6, SEQ ID NO:7 and/or SEQ ID NO: 8; oligonucleotides being complementary to the oligonucleotides according to SEQ ID NO:3, SEQ ID NO:4, SEQ ID NO:5, SEQ ID NO:6, SEQ ID NO:7 and/or SEQ ID NO: 8; oligonucleotides comprising any one of the aforementioned oligonucleotides and being elongated by not more than 5 base pairs compared to the oligonucleotides according to SEQ ID NO:3, SEQ ID NO:4, SEQ ID NO:5, SEQ ID NO:6, SEQ ID NO:7 and/or SEQ ID NO: 8. Preferably, the kit comprises at least two primers or at least four primers. A kit comprising two primers and one probe or a kit comprising for primers and two probes is particularly preferred. The kit may further comprise buffer solutions, such as PCR buffer; magnesia salts; deoxy nucleotide triphosphates (dNTPs). The kit may also include elements such as sample collection tubes, reagents to isolate the nucleic acids and/or instructions for its use.

In addition to the above, the present inventors have unexpectedly found that an increased level of netB marker gene, homologues and fragments thereof, in comparison to a non-infected control and an increase in the level of netB over time, respectively, is an indication of necrotic enteritis.

Accordingly, the present invention also pertains to a method for detecting avian necrotic enteritis, the method comprising
a) collecting excremental samples of a specific avian or of a specific avian population at consecutive points in time; and
b) monitoring the level of marker gene netB and/or homologues and fragments thereof in these samples;
wherein an increase in the level of the marker gene constitutes an indication of avian necrotic enteritis.

In a preferred embodiment of the aforementioned method, the present invention also pertains to a method for detecting avian necrotic enteritis, Method for detecting avian necrotic enteritis, the method comprising
a) collecting excremental samples of a specific avian or of a specific avian population at consecutive points in time; and
b) monitoring the level of marker gene netB in these samples;
wherein an increase in the level of netB constitutes an indication of avian necrotic enteritis.

In that regard and in accordance with common understanding, an increase of about 0.2 to 0.3 log (i.e. factor two to five) is to be considered relevant.

The inventors have found that an amount of netB of at least $10^7$ copies/g feces constitutes an indication of necrotic enteritis.

Accordingly, the present invention also pertains to a method for detecting avian necrotic enteritis, the method comprising
a) collecting excremental samples of a specific avian or of a specific avian population at consecutive points in time; and
b) monitoring the level of marker gene netB in these samples;
wherein an amount of netB of at least $10^7$ copies/g feces constitutes an indication of necrotic enteritis.

The above methods are suitable for detecting both, clinical and sub-clinical/latent states of necrotic enteritis.

Surprisingly, the inventors also have found that the amount of netB marker gene correlates with the extent of intestinal lesions of the corresponding avian subject and thus with the grade of necrotic enteritis. Accordingly, the present invention is also directed to a method for determining the grade of avian necrotic enteritis, the method comprising determining the amount of netB marker gene and/or homologues and fragments thereof, in avian excremental samples, wherein the amount of said marker gene indicates the grade of necrotic enteritis.

In the above methods, the oligonucleotide primers and probes described in the following turned out to be particularly effective.

Accordingly, oligonucleotides selected from the group consisting of
a) oligonucleotides having a sequence identity of at least 80%, preferably at least 85, 90 or 95%, most preferably 100%, to the polynucleotide as depicted in SEQ ID NO:3;

b) oligonucleotides having a sequence identity of at least 80%, preferably at least 85, 90 or 95%, most preferably 100%, to the polynucleotide as depicted in SEQ ID NO: 4;

c) oligonucleotides having a sequence identity of at least 80%, preferably at least 85, 90 or 95%, most preferably 100%, to the polynucleotide as depicted in SEQ ID NO: 5;

d) oligonucleotides being complementary to the oligonucleotides according to (a) to (c);

e) oligonucleotides comprising any one of the oligonucleotides according to (a) to (d) and being elongated by not more than 5 base pairs compared to the oligonucleotides according to (a) to (d);

may be used in one of the above-described methods for detecting avian necrotic enteritis as a PCR primer and/or as a PCR probe for detecting netB.

The polynucleotide as depicted in SEQ ID NO: 3 is a PCR primer (fwd) for detecting netB. The polynucleotide as depicted in SEQ ID NO: 4 is a PCR primer (rev) for detecting netB. The polynucleotide as depicted in SEQ ID NO: 5 is a PCR probe for detecting netB.

The present invention further provides a diagnostic kit for determining whether or not an avian population, such as an avian flock, suffers from (sub-clinical) necrotic enteritis. Said kit comprises a set of oligonucleotides for amplifying and/or quantifying the polynucleotide encoding the netB marker gene. In a preferred embodiment, the kit comprises one or more oligonucleotides having a sequence identity of at least 80%, preferably at least 85, 90 or 95%, most preferably 100%, to one or more of the polynucleotides as depicted SEQ ID NO:3, SEQ ID NO:4 and/or SEQ ID NO:5; oligonucleotides being complementary to the oligonucleotides according to SEQ ID NO:3, SEQ ID NO:4 and/or SEQ ID NO:5; oligonucleotides comprising any one of the aforementioned oligonucleotides and being elongated by not more than 5 base pairs compared to the oligonucleotides according to SEQ ID NO:3, SEQ ID NO:4 and/or SEQ ID NO:5. Preferably, the kit comprises two primers. A kit comprising two primers and one probe is particularly preferred. The kit may further comprise buffer solutions, such as PCR buffer; magnesia salts; deoxy nucleotide triphosphates (dNTPs). The kit may also include elements such as sample collection tubes, reagents to isolate the nucleic acids and/or instructions for its use.

The present invention provides the above-described non-invasive methods for detecting avian necrotic enteritis and for determining the grade of necrotic enteritis which can be performed ante mortem. This enables the farmer to efficiently treat the avian population suffering from necrotic enteritis, if necessary, subsequently after having performed the above-mentioned test. Alternatively or additionally, the farmer may also administer health-promoting substances, such as zootechnical feed additives.

Preferably, the therapeutic agent or the health-promoting substance is selected from the group consisting of antibiotic agents, probiotic agents, praebiotic agents, organic/fatty acids, bacteriophages and bacteriolytic enzymes.

In accordance therewith, the present invention is also directed to antibiotic agents for use in the treatment of necrotic enteritis, wherein the necrotic enteritis is detected or evaluated by performing one of the methods indicted above. Moreover, the present invention is directed to the use of probiotic agents, praebiotic agents organic/fatty acids, bacteriophages and bacteriolytic enzymes for ameliorating the health status of an animal or an animal population.

Applications of the methods according to the invention are for example (i) aiding in the diagnosis and/or prognosis of C. perfringens induced diseases, such as avian necrotic enteritis, (ii) monitoring the progress or reoccurrence of these diseases, (iii) aiding in the evaluation of treatment efficacy for an animal population undergoing or contemplating treatment, or (iv) controlling (therapeutic) vaccination efficiency against C. perfringens induced diseases.

Applications of the invention in particular help to avoid loss in animal performance like weight gain and feed conversion.

In the following, the invention is illustrated by non-limiting examples and exemplifying embodiments.

EXAMPLES

1. In Vivo Model

A sub-clinical in vivo model for necrotic enteritis was used. In this model Ross 308 broilers (female and male) were grouped with 27 birds per group. They were fed a wheat/rye (43%/7.5%) based diet, with soybean meal as protein source until day 16. From day 17 onwards, soybean meal was replaced by fishmeal (30%) as protein source. At day 4 and 9 the broilers were orally inoculated with Poulvac Bursa Plus (Zoetis) as immunosuppressant. At day 14 and 16, the broilers were orally inoculated with a ten-fold dose of Hipracox.

The birds of 5 groups (P.A-P.E) were three times per day challenged orally with approximately $4 \times 10^8$ cfu netB-positive, pathogenic C. perfringens (late-log culture) bacteria (Cp56) for two consecutive days (day 18 and 19). Two groups of birds (P.F and P.G) were challenged only one time per day, to induce milder necrotic lesions than the previous groups challenged three times per day.

The chickens were challenged for two consecutive days. All animals were euthanized at day 20. Intestinal lesions in the small intestine (duodenum to ileum) were scored as follows: 0=no gross lesions; 1=congested intestinal mucosa; 2=small focal necrosis or ulceration (1-5 foci); 3=focal necrosis or ulceration (6-15 foci); 4=focal necrosis or ulceration (16 or more foci); 5=patches of necrosis 2-3 cm long; 6=diffuse necrosis typical of field cases. Non-infected control birds were treated in the same manner except for the inoculation with C. perfringens. These control birds were inoculated with sterile bacterial growth medium (BHI-broth).

None of the negative control birds, receiving sterile bacterial medium (BHI) instead of the pathogenic C. perfringens culture developed necrotic enteritis. Also the birds challenged with a non-pathogenic C. perfringens strain were free of necrotic lesions. In the other groups, challenged with pathogenic Cp56, most birds developed necrotic enteritis. With a high amount of birds showing severe lesions.

Summary of the In Vivo Model:

|  | D4 | D9 | D14 | D16 | D17 | D18 | D19 | D20 |
|---|---|---|---|---|---|---|---|---|
| Poulvac Bursa Plus | x | X |  |  |  |  |  |  |
| Hipracox × 10 |  |  | x | X |  |  |  |  |
| Feed + fishmeal |  |  |  |  | x | x | x |  |
| Inoculation C. perfringens |  |  |  |  |  | x | x |  |
| Scoring |  |  |  |  |  |  |  | x |

Fresh cloacal samples (i.e. samples of individual animals) were collected immediately after death and snap frozen in liquid $N_2$ prior to storage at −80° C.

Cloacal samples of individualized animals:
Infected birds (different lesion scores)
non-infected control groups
birds inoculated with netB-negative *C. perfringens*

Litter samples (=mixed fecal droppings in the pen, i.e. pooled samples of the avian flock) were collected from each group using the overshoe method (only day 19) and using litter grabs at 5 different places in the pen from the day before inoculation (day 17) until day 19.

Types and amounts of samples collected:

| | SAMPLE | AMOUNT OF SAMPLES |
|---|---|---|
| CLOACAL SAMPLES | Non-infected | 10 |
| | Infected with netB-negative *C. perfringens* | 10 |
| LITTER SAMPLES | Score 0 | 10 |
| | Score 2 | 10 |
| | Score 3 or 4 | 10 |
| | Score 5 or 6 | 8 |
| | Non-infected (BHI) | |
| | Before inoculation | 1 litter grab |
| | After first inoculation | 1 litter grab |
| | After second inoculation | 1 litter grab + 1 shoe cover sample |
| | Infected with Non-pathogenic *C. perfringens* | |
| | Before inoculation | 2 litter grabs |
| | After first inoculation | 2 litter grabs |
| | After second inoculation | 2 litter grabs + 2 shoe cover samples |
| | Infected with netB-positive *C. perfringens* | |
| | Before inoculation | 7 litter grabs |
| | After first inoculation | 7 litter grabs |
| | After second inoculation | 7 litter grabs + 6 shoe cover samples |

Shoe cover samples were collected only at day 19. Litter samples were collected on day 17 until day 19. The samples were homogenized and split in three portions.

2. DNA Extraction and Quantification

DNA was extracted from the samples using the CTAB method. Therefore, 100 mg of cloacal material and 200 mg of litter grab or shoe cover sample was used as starting material. The total DNA was eluted in 100 μl water. The DNA concentration was determined with a Nanodrop ND 1000 spectrophotometer (Nanodrop Technologies, Wilmington, Del., USA) and adjusted to a final concentration of 50 ng/μl.

qPCR was performed using SYBR-green 2× master mix (Bioline, Brussels, Belgium) in a Bio-Rad CFX-384 system. Each reaction was done in triplicate in a 12 μL total reaction mixture using 2 μL of the DNA sample and 0.5 μM final qPCR primer concentration. The qPCR conditions used were the same for both genes: 1 cycle of 95° C. for 10 min, followed by 40 cycles of 95° C. for 30 s, 60° C. for 30 s, and stepwise increase of the temperature from 65° to 95° C. (at 10s/0.5° C.). Melting curve data were analyzed to confirm the specificity of the reaction. For construction of the standard curve, the PCR product was generated using the standard PCR primers listed below and DNA from *C. perfringens* strain CP56. After purification (MSB Spin PCRapace, Stratec Molecular, Berlin, Germany) and determination of the DNA concentration. The concentration of the linear dsDNA standard was adjusted to $1\times10^7$ to $1\times10^1$ copies per μL with each step differing by 10 fold. The copy numbers of samples were determined by reading off the standard series with the Ct values of the samples.

The detection limit of the qPCR technique is dependent on the DNA concentration obtained after CTAB extraction and was around $10^5$ gene copies/g material.

Primers used in the PCR assay:

| | PCR | | |
|---|---|---|---|
| cpa | AGT CTA CGC TTG GGA TGG AA | (fwd) | SEQ ID NO: 9 |
| | TTT CCT GGG TTG TTC ATT TC | (rv) | SEQ ID NO: 10 |

-continued

| | | | |
|---|---|---|---|
| netB | TGA TAC CGC TTC ACA TAA AGG T | (fwd) | SEQ ID NO: 11 |
| | ACC GTC CTT AGT CTC AAC AAA T | (rv) | SEQ ID NO: 12 |
| | qPCR | | |
| cpa | GTT GAT AGC GCA GGA CAT GTT AAG | (fwd) | SEQ ID NO: 13 |
| | CAT GTA GTC ATC TGT TCC AGC ATC | (rv) | SEQ ID NO: 14 |
| netB | TCA ATT GGT TAT TCT ATA GGC GGT A | (fwd) | SEQ ID NO: 15 |
| | ATA TGA AGC ATT TAT TCC AGC ACC A | (rv) | SEQ ID NO: 16 |

3. Aggregate Testing: Correlating the Amount of Marker Genes in Cloacal Samples of Individualized Animals In these Examples, the above-mentioned cloacal samples were investigated.

At the day of necropsy the alpha toxin gene (cpa) was present in cloacal samples from all groups (both uninfected and infected birds) and also the netB gene was present in all cloacal samples.

3.1 Correlation of the Amount of netB with Lesion Score

Only in cloacal samples from birds challenged with a pathogenic, netB positive *C. perfringens* strain, the mean netB signal is above $10^7$ copies/g feces.

|  | netB [copies/ g sample] | netB [Log copies/ g sample] | standard deviation |
|---|---|---|---|
| Non-infected (BHI) | 3.16E+06 | 6.50 | 0.37 |
| Non-path. Cp | 3.92E+06 | 6.59 | 0.32 |
| Score 0 | 1.16E+08 | 8.06 | 0.54 |
| Score 2 | 4.96E+08 | 8.70 | 0.73 |
| Score 3-4 | 7.18E+08 | 8.86 | 0.79 |
| Score 5-6 | 4.83E+09 | 9.68 | 0.64 |

This Example shows that the amount of netB gene in the analyzed samples directly correlates with the intestinal lesion score of the analyzed bird, i.e. with the grade of necrotic enteritis of the infected bird.

The correlation between the lesion scores from the birds infected with the pathogenic *C. perfringens* strain and the amount of the genes (netB/cpa) present in the feces was calculated by spearman correlation. The spearman r-value can range from 0 to 1: r=1→perfect correlation, r=0→no correlation. The presence of all tested genes show a correlation with the disease severity, with the highest correlation with the netB gene.

|  | copies/g sample | | Log copies/g sample | | standard deviation | |
|---|---|---|---|---|---|---|
|  | netB | cpa | netB | cpa | netB | cpa |
| Non-infected (BHI) | 3.16E+06 | 3.72E+08 | 6.50 | 8.57 | 0.37 | 0.87 |
| Non-path. Cp | 3.92E+06 | 6.59E+07 | 6.59 | 7.82 | 0.32 | 0.95 |
| Score 0 | 1.16E+08 | 2.81E+08 | 8.06 | 8.45 | 0.54 | 0.48 |
| Score 2 | 4.96E+08 | 4.44E+08 | 8.70 | 8.65 | 0.73 | 0.77 |
| Score 3-4 | 7.18E+08 | 1.33E+09 | 8.86 | 9.12 | 0.79 | 0.62 |
| Score 5-6 | 4.83E+09 | 1.93E+09 | 9.68 | 9.29 | 0.64 | 0.75 |

Spearman-Calculation:

| Parameter | cpa | netB |
|---|---|---|
| Number of XY Pairs | 38 | 38 |
| Spearman r | 0.4195 | 0.6110 |
| 95% confidence interval | 0.1055 to 0.6574 | 0.3534 to 0.7825 |
| P value (two-tailed) | 0.0088 | P < 0.0001 |
| P value summary | ** | *** |
| Exact or approximate P value? | Gaussian Approximation | Gaussian Approximation |
| Is the correlation significant? (alpha = 0.05) | Yes | Yes |

The Spearman correlation provides mathematical prove on the correlation between the amount of netB in the cloacal sample and the grade of necrotic enteritis.

3.2 Correlation netB/Cpa Ratio with Lesion Score

The ratio of netB gene versus the cpa gene in the cloacal samples of non-infected birds (BHI), birds challenged with the non-pathogenic strain (Non-path) and birds challenged with the pathogenic *C. perfringens* strain were investigated.

The birds showed different degrees of disease severity (score 0 to score 5 to 6):

|  | Mean ratio netB/cpa |
|---|---|
| Non-infected (BHI) | 0.04 |
| Non-path. Cp | 0.09 |
| Score 0 | 0.83 |

|  | Mean ratio netB/cpa |
|---|---|
| Score 2 | 1.85 |
| Score 3-4 | 1.27 |
| Score 5-6 | 2.69 |

4. Bulk Testing: Monitoring the Amount of Marker Genes in Excremental Samples of the Avian Population Over Time In these Examples, the litter samples indicated above were investigated.

4.1 Monitoring the Amount of netB Over Time

It was found that the amount of netB gene in the litter samples significantly increased starting from the day following the day of inoculation (day 18) with the pathogenic *C. perfringens* strain:

|  | netB copies/ g sample | Log copies/g sample | standard deviation |
|---|---|---|---|
| Non-infected (BHI) - day 17 | 1.97E+05 | 5.29 |  |
| Non-infected (BHI) - day 18 | 2.53E+05 | 5.40 |  |
| Non-infected (BHI) - day 19 | 1.12E+05 | 5.05 |  |
| Non-infected (BHI) - day 19 - BS | 8.46E+04 | 4.93 |  |
| Non-path. Cp - day 17 | 6.92E+04 | 4.84 | 0.09 |
| Non-path. Cp - day 18 | 4.17E+04 | 4.62 | 0.05 |
| Non-path. Cp - day 19 | 8.01E+04 | 4.90 |  |
| Non-path. Cp - day 19 - BS | 4.16E+04 | 4.62 | 0.39 |
| NE-group - day 17 | 3.21E+05 | 5.51 | 0.93 |
| NE-group - day 18 | 7.03E+07 | 7.85 | 0.74 |
| NE-group - day 19 | 1.11E+08 | 8.05 | 0.24 |
| NE-group - day 19 - BS | 2.63E+08 | 8.42 | 0.95 |

4.2 Monitoring the netB/Cpa Ratio Over Time

It was found that the ratio of netB gene versus the cpa gene in the litter samples collected at days 17 to 19 significantly increased starting from the day following the day of inoculation (day 18) with the pathogenic *C. perfringens* strain:

|  | netB/cpa |
|---|---|
| Non-infected (BHI) - day 17 | 0.00 |
| Non-infected (BHI) - day 18 | 0.01 |
| Non-infected (BHI) - day 19 | 0.00 |
| Non-infected (BHI) - day 19 - BS | 0.00 |
| Non-path. Cp - day 17 | 0.00 |
| Non-path. Cp - day 18 | 0.00 |
| Non-path. Cp - day 19 | 0.00 |
| Non-path. Cp - day 19 - BS | 0.00 |
| NE-group - day 17 | 0.08 |
| NE-group - day 18 | 1.27 |
| NE-group - day 19 | 2.45 |
| NE-group - day 19 - BS | 2.63 |

The above experiments show that an increase in the amount of netB gene and in the ratio of netB/cpa genes, respectively, in pooled animal excremental samples collected in consecutive points in time, correlates with the development or the progression of necrotic enteritis. Therewith, it is proven that the methods of the present invention allow an assessment of the health status of a whole animal flock regarding *C. perfringens* induced diseases.

The invention claimed is:

1. A method for detecting and then treating *C. perfringens* induced diseases in animals, comprising:
    a) collecting sample material of a specific animal at consecutive points in time or of a specific group of animals at consecutive points in time;
    b) determining the amount of a first marker and a second marker contained in the sample material; and
    c) determining the ratio of the first marker to the second marker contained in the sample material;
    wherein the first marker is a gene specific for a disease-inducing *C. perfringens* bacterium selected from the group consisting of:
        i) cpe toxin (cpe); cpe homologues that are at least 90% identical to wildtype cpe; and cpe fragments that, relative to the wildtype cpe, are truncated by not more than 100 nucleotides;
        ii) beta-toxin (cpb); cpb homologues that are at least 90% identical to wildtype cpb; and cpb fragments that, relative to the wildtype cpb, are truncated by not more than 100 nucleotides;
        iii) epsilon toxin (etx); homologues that are at least 90% identical to wildtype etx; and etx fragments that, relative to the wildtype etx, are truncated by not more than 100 nucleotides;
        iv) netF toxin (netF); netF homologues that are at least 90% identical to wildtype netF; and netF fragments that, relative to the wildtype netF, are truncated by not more than 100 nucleotides;
        v) netB toxin (netB); homologues that are at least 90% identical to wildtype netB; and netB fragments that, relative to the wildtype netB, are truncated by not more than 100 nucleotides;
    and the second marker comprises a polynucleotide specific for the species *C. perfringens*; and
    wherein an increase in the ratio of the first marker to the second marker in the analyzed sample material over time is an indication of *C. perfringens* induced disease;
    d) administering a therapeutic agent or a health-promoting substance to animals identified in step c) as having *C. perfringens* induced disease, wherein said therapeutic agent or health-promoting substance is selected from the group consisting of: an antibiotic agent; a probiotic agent; a prebiotic agent; an organic/fatty acid; a bacteriophage; and a bacteriolytic enzyme.

2. The method of claim 1, wherein the first marker is located on a toxin plasmid of *C. perfringens* and the second marker is located on the *C. perfringens* chromosome.

3. The method of claim 2, wherein the second marker is cpa.

4. The method of claim 3, wherein the sample material is obtained from an avian flock.

5. The method of claim 1, wherein the second marker is cpa.

6. The method of claim 5, wherein the sample material is obtained from an avian flock.

7. The method of claim 1, wherein the sample material is a pooled sample selected from the group consisting of: dust samples; litter samples; liquid manure samples; fur samples; feather samples; skin samples; samples of bodily excrements; and solutions or suspensions thereof.

8. The method of claim 1, wherein the sample material is pooled feces.

9. The method of claim 1, wherein the first marker and the second marker in the sample material are detected and quantified by PCR.

10. The method of claim 1, wherein the *C. perfringens* induced disease is necrotic enteritis.

11. The method of claim 10, wherein the necrotic enteritis is in a sub-clinical or latent state.

12. The method of claim 1, wherein the first marker is netB, the second marker is cpa and the *C. perfringens* induced disease is necrotic enteritis.

13. The method of claim 12, wherein said first marker and said second marker are quantitated by PCR using a PCR primer and/or a PCR probe selected from the group consisting of:
    a) oligonucleotides comprising a sequence identity of at least 80% to the polynucleotide of SEQ ID NO:3;
    b) oligonucleotides comprising a sequence identity of at least 80% to the polynucleotide of SEQ ID NO:4;
    c) oligonucleotides comprising a sequence identity of at least 80% to the polynucleotide of SEQ ID NO:5;
    d) oligonucleotides comprising a sequence identity of at least 80% to the polynucleotide of SEQ ID NO:6;
    e) oligonucleotides comprising a sequence identity of at least 80% to the polynucleotide of SEQ ID NO:7;
    f) oligonucleotides comprising a sequence identity of at least 80% to the polynucleotide of SEQ ID NO:8;
    g) oligonucleotides that are complementary to the full length of one or more oligonucleotides of paragraphs (a) to (f).

14. The method of claim 13, wherein the oligonucleotides of paragraphs a)-h) are selected from the group consisting of:
    a) oligonucleotides comprising a 100% sequence identity to the polynucleotide of SEQ ID NO:3;
    b) oligonucleotides comprising a 100% sequence identity to the polynucleotide of SEQ ID NO:4;
    c) oligonucleotides comprising a 100% sequence identity to the polynucleotide of SEQ ID NO:5;
    d) oligonucleotides comprising a 100% sequence identity to the polynucleotide of SEQ ID NO:6;
    e) oligonucleotides comprising a 100% sequence identity to the polynucleotide of SEQ ID NO:7;
    f) oligonucleotides comprising a 100% sequence identity to the polynucleotide of SEQ ID NO:8;
    g) oligonucleotides that are complementary to the full length of one or more oligonucleotides of paragraphs (a) to (f).

15. The method of claim 12, wherein said method is carried out using a diagnostic kit comprising at least one primer and at least one probe for detecting netB and cpa.

16. The method of claim 15, wherein said at least one primer and said at least one probe for detecting netB and cpa comprise one or more oligonucleotides selected from the group consisting of:
a) oligonucleotides comprising a sequence identity of at least 80% to the polynucleotide of SEQ ID NO:3;
b) oligonucleotides comprising a sequence identity of at least 80% to the polynucleotide of SEQ ID NO:4;
c) oligonucleotides comprising a sequence identity of at least 80% to the polynucleotide of SEQ ID NO:5;
d) oligonucleotides comprising a sequence identity of at least 80% to the polynucleotide of SEQ ID NO:6;
e) oligonucleotides comprising a sequence identity of at least 80% to the polynucleotide of SEQ ID NO:7;
f) oligonucleotides comprising a sequence identity of at least 80% to the polynucleotide of SEQ ID NO:8;
g) oligonucleotides that are complementary to the full length of one or more oligonucleotides of paragraphs (a) to (f).

17. The method of claim 16, wherein said oligonucleotides are selected from the group consisting of:
a) oligonucleotides comprising a 100% sequence identity to the polynucleotide of SEQ ID NO:3;
b) oligonucleotides comprising a 100% sequence identity to the polynucleotide of SEQ ID NO:4;
c) oligonucleotides comprising a 100% sequence identity to the polynucleotide of SEQ ID NO:5;
d) oligonucleotides comprising a 100% sequence identity to the polynucleotide of SEQ ID NO:6;
e) oligonucleotides comprising a 100% sequence identity to the polynucleotide of SEQ ID NO:7;
f) oligonucleotides comprising a 100% sequence identity to the polynucleotide of SEQ ID NO:8;
g) oligonucleotides that are complementary to the full length of one or more oligonucleotides of paragraphs (a) to (f).

18. The method of claim 12, wherein the sample material is obtained from an avian flock and is a pooled sample selected from the group consisting of: dust samples; litter samples; liquid manure samples; feather samples; skin samples; samples of bodily excrements; and solutions or suspensions thereof.

19. The method of claim 18, wherein the first marker and the second marker in the sample material are detected and quantified by PCR and the *C. perfringens* induced disease is necrotic enteritis.

* * * * *